US007939490B2

(12) United States Patent
Winkles et al.

(10) Patent No.: US 7,939,490 B2
(45) Date of Patent: May 10, 2011

(54) TWEAK AS A THERAPEUTIC TARGET FOR TREATING CENTRAL NERVOUS SYSTEM DISEASES ASSOCIATED WITH CEREBRAL EDEMA AND CELL DEATH

(75) Inventors: Jeffrey A. Winkles, Frederick, MD (US); Manuel S. Yepes, Atlanta, GA (US)

(73) Assignee: University of Maryland, Baltimore, Baltimore, MD (US)

( * ) Notice: Subject to any disclaimer, the term of this patent is extended or adjusted under 35 U.S.C. 154(b) by 560 days.

(21) Appl. No.: 11/718,786

(22) PCT Filed: Nov. 8, 2005

(86) PCT No.: PCT/US2005/040360
§ 371 (c)(1),
(2), (4) Date: May 7, 2007

(87) PCT Pub. No.: WO2006/052926
PCT Pub. Date: May 18, 2006

(65) Prior Publication Data
US 2007/0280940 A1 Dec. 6, 2007

Related U.S. Application Data

(60) Provisional application No. 60/636,024, filed on Dec. 13, 2004, provisional application No. 60/626,054, filed on Nov. 8, 2004.

(51) Int. Cl.
*A61K 39/44* (2006.01)
*A61K 39/395* (2006.01)
*A61K 38/16* (2006.01)
*A61K 38/18* (2006.01)
*A61P 25/00* (2006.01)

(52) U.S. Cl. .................. 514/1.1; 424/133.1; 424/134.1; 424/141.1; 424/143.1; 424/145.1; 424/178.1; 514/7.6; 514/12.2; 514/13.3; 514/17.7; 514/21.2

(58) Field of Classification Search ........................ None
See application file for complete search history.

(56) References Cited

U.S. PATENT DOCUMENTS

| | | | |
|---|---|---|---|
| 5,149,655 A | 9/1992 | McCabe et al. | |
| 5,206,152 A | 4/1993 | Sukhatme | |
| 5,422,120 A | 6/1995 | Kim | |
| 5,580,859 A | 12/1996 | Felgner et al. | |
| 5,919,619 A | 7/1999 | Tullis | |
| 7,169,387 B2 * | 1/2007 | Rennert | 424/145.1 |
| 7,482,430 B2 * | 1/2009 | Wiley | 530/350 |
| 2006/0240004 A1 * | 10/2006 | Burkly et al. | 424/143.1 |
| 2009/0053211 A9 * | 2/2009 | Lazar et al. | 424/133.1 |
| 2009/0068102 A1 | 3/2009 | Burkly et al. | |

FOREIGN PATENT DOCUMENTS

| | | |
|---|---|---|
| EP | 524968 | 10/1991 |
| WO | 90/11092 | 10/1990 |
| WO | 91/14445 | 10/1991 |
| WO | 92/11033 | 7/1992 |
| WO | 94/23697 | 10/1994 |
| WO | 95/13796 | 5/1995 |
| WO | 99/14346 | 3/1999 |
| WO | WO 00/42073 | 7/2000 |
| WO | 01/29058 | 4/2001 |
| WO | WO 2006/130374 | 12/2006 |

OTHER PUBLICATIONS

Ballabh P et al. The blood-brain barrier: an overview. Structure, regulation, and clinical implications. Neurobiology Disease, 2004; 16:1-13.*
Chu K et al. Celevoxib induces functional recovery after intracerebral hemorrhage with reduction of brain edema and perihematomal cell death. J Cereb Blood Flow Metab. Aug. 2004; 24(8):926-933; abstract only.*
Alberts B et al. Molecular Biology of the Cell, Fourth Edition, 2002, Garland Science, p. 129.*
International Search Report and Written Opinion, International Patent Application No. PCT/US05/40360, Issued May 8, 2006.
Aggoun-Zouaoui, D., et al., "Ultrastructural Morphology of Neuronal Death Following Reversible Focal Ischemia in the Rat," Apoptosis, 3:133-141, (1998).
Asahi, M., et al., "Role for Matrix Metalloproteinase 9 After Focal Cerebral Ischemia: Effects of Gene Knockout and Enzyme Inhibition with BB-94," J. Cereb. Blood Flow and Metab., 20:1681-1689, (2000).
Asahi, M., et al., "Effects of Matrix Metalloproteinase-9 Gene Knock-Out on the Proteolysis of Blood-Brain Barrier and White Matter Components After Cerebral Ischemia," The Journal of Neuroscience, 21(19):7724-7732, (2001).
Backskai, B.J., et al., "The Endocytic Receptor Protein LRP Also Mediates Neuronal Calcium Signaling Via N-Methyl-D-Aspartate Receptors," PNAS, 97(21):11551-11556, (2000).
Baker, R.N., et al., "The Movement of Exogenous Protein in Experimental Cerebral Edema," J. Neuropathol. Exp. Neurol., 30:668-679, (1971).
Barber, P.A., et al., "Biochemistry of Ischemic Stroke," Advances in Neurology, 92:151-164, (2003).
Bolton, S.J., et al., "Loss of the Tight Junction Proteins Occludin and Zonula Occludens-1 from Cerebral Vascular Endothelium During Neutrophil-Induced Blood-Brain Barrier Breakdown In Vivo," Neuroscience, 86(4):1245-1257, (1998).
Brown, S.A., et al., "The Fn14 Cytoplasmic Tail Binds Tumour-Necrosis-Factor-Receptor-Associated Factors 1, 2, 3, and 5 and Mediates Nuclear Factor-κB Activation," Biochem. Journal, 371:395-403, (2003).

(Continued)

*Primary Examiner* — Elizabeth C. Kemmerer
*Assistant Examiner* — Kimberly A. Ballard
(74) *Attorney, Agent, or Firm* — DLA Piper LLP US

(57) ABSTRACT

The present invention is directed to compositions and methods for treating cerebral edema and cell death in neurological conditions characterized by disruption of the architecture of the neurovascular unit with increase in the permeability of the NVU, particularly for treating stroke. One aspect of the present invention relates to a composition comprising an agent that interferes with a TWEAK-mediated signaling pathway. Another aspect of the present invention relates to a method of using a composition which comprises an agent that inhibits Fn14 activity or Fn14 expression for the prevention and/or treatment of cerebral edema and cell death occurring in certain neurological conditions such as cerebral ischemia.

26 Claims, 24 Drawing Sheets

OTHER PUBLICATIONS

Carson, M.P., et al., "Microvascular Endothelium and Pericytes: High Yield, Low Passage Cultures," In Vitro Cell & Dev. Biol., 22(6):344:354, (1986).

Chen, Z., et al., "Brain Capillary Endothelial Cells Express MBEC1, a Protein that is Related to the *Clostridium perfringens* Enterotoxin Receptors," Laboratory Investigation, 78(3):353-363, (1998).

Chicheportiche, Y., et al., "TWEAK, a New Secreted Ligand in the Tumor Necrosis Factor Family that Weakly Induces Apoptosis," The Journal of Biological Chemistry, 272(51):32401-32410, (1997).

Curiel, D.T., et al., "High-Efficiency Gene Transfer Mediated by Adenovirus Coupled to DNA-Polylysine Complexes," Human Gene Therapy, 3:147-154, (1992).

Desplat-Jégo, S., et al., "TWEAK Is Expressed by Glial Cells, Induces Astrocyte Proliferation and Increases EAE Severity," Journal of Neuroimmunology, 133:116-123, (2002).

Dirnagl, U., et al., "Pathobiology of Ischaemic Stroke: An Integrated View," Trends Neurosci., 22(9):391-397, (1999).

Dereski, M.O., et al., "The Heterogeneous Temporal Evolution of Focal Ischemic Neuronal Damage in the Rat," Acta Neuropathol. (Berl.), 85:327-333, (1993).

Donohue, P.J., et al., "TWEAK is an Endothelial Cell Growth and Chemotactic Factor that Also Potentiates FGF-2 and VEGF-A Mitogenic Activity," Arterioscler. Throm. Vasc. Biol., 23:594-600, (2003).

Feng, S.L.Y., et al., "The Fn14 Immediate-Early Response Gene is Induced During Liver Regeneration and Highly Expressed in Both Human and Murine Hepatocellular Carcinomas," American Journal of Pathology, 156(4):1253-1261, (2000).

Fischer, D., et al., "Switching Mature Retinal Ganglion Cells to a Robust Growth State In Vivo: Gene Expression and Synergy with RhoA Inactivation," The Journal of Neuroscience, 24(40):8726-8740, (2004).

Flaris, N.A., et al., "Characterization of Microglia and Macrophages in the Central Nervous System of Rats: Definition of the Differential Expression of Molecules Using Standard and Novel Monoclonal Antibodies in Normal CNS and in Four Models of Parenchymal Reaction," Glia, 7:34-40, (1993).

Garcia, J.H., et al., "Neuronal Ischemic Injury: Light Microscopy, Ultrastructure and Biochemistry," Acta Neuropathol. (Berl), 43:85-95, (1978).

Hakim, A.M., "The Cerebral Ischemic Penumbra," Le Journal Canadien Des Sciences Neurologiques, 14(4):557-559, (1987).

Han, S., et al., "TNF-Related Weak Inducer of Apoptosis Receptor, a TNF Receptor Superfamily Member, Activates NF-κB Through TNF Receptor-Associated Factors," Biochem. Biophys. Res. Commun., 305:789-796, (2003).

Harada, N. et al., "Pro-Inflammatory Effect of TWEAK/Fn14 Interaction on Human Umbilical Vein Endothelial Cells," Biochem. Biophys. Res. Commun., 299:488-493, (2002).

Huckett, B., et al., "Evidence for Targeted Gene Transfer by Receptor-Mediated Endocytosis," Biochem. Pharmacol., 40(2):253-263, (1990).

Jin, L., et al., "Induction of RANTES by TWEAK/Fn14 Interaction in Human Keratinocytes," The Journal of Investigative Dermatology, 122:1175-1179, (2004).

Kaltschmidt, C., et al., "Constitutive NF-κB Activity in Neurons," Molecular and Cellular Biology, 14(6):3981-3992, (1994).

Kato, H., et al., "Progressive Expression of Immunomolecules on Activated Microglia and Invading Leukocytes Following Focal Cerebral Ischemia in the Rat," Brain Research, 734:203-212, (1996).

Kawakita, T., et al., "Functional Expression of TWEAK in Human Hepatocellular Carcinoma: Possible Implication in Cell Proliferation and Tumor Angiogenesis," Biochem. Biophys. Res. Commun., 318:726-733, (2004).

Kim, S.H., et al., "TWEAK Can Induce Pro-Inflammatory Cytokines and Matrix Metalloproteinase-9 in Macrophages,". Circ. J., 68:396-399, (2004).

Lee, J.M., et al., "The Changing Landscape of Ischaemic Brain Injury Mechanisms," Nature, 399:A7-14, (1999).

Lee, Y.B., et al., "Cytokines, Chemokines, and Cytokine Receptors in Human Microglia," Journal of Neuroscience Research, 69:94-103, (2002).

Lehrmann, E., et al., "Microglia and Macrophages are Major Sources of Locally Produced Transforming Growth Factor-β1 After Transient Middle Cerebral Artery Occlusion in Rats," Glia, 24:437-448, (1998).

Lynch, C.N., et al., "TWEAK Induces Angiogenesis and Proliferation of Endothelial Cells," The Journal of Biological Chemistry, 274(13):8455-8459, (1999).

Maratea, D., et al., "Deletion and Fusion Analysis of the Phage ⌀X174 Lysis Gene E," Gene, 40:39-46, (1985).

Matsumoto, T., et al., "Prevention of Cerebral Edema and Infarct in Cerebral Reperfusion Injury by an Antibody to Interleukin-8," Laboratory Investigation, 77(2):119-125, (1997).

Mattson, M.P., et al., "NF-κB in Neuronal Plasticity and Neurodegenerative Disorders," The Journal of Clinical Investigation, 107(3):247-254, (2001).

McCarthy, K.D., et al., "Preparation of Separate Astroglial and Oligodendroglial Cell Cultures from Rat Cerebral Tissue," J. Cell Biol., 85:890-902, (1980).

Meighan-Mantha, R.L., et al., "The Mitogen-Inducible Fn14 Gene Encodes a Type I Transmembrane Protein that Modulates Fibroblast Adhesion and Migration," The Journal of Biological Chemistry, 274(46):33166-33176, (1999).

Meng, X., et al., "Characterizing the Diffusion/Perfusion Mismatch in Experimental Focal Cerebral Ischemia," Annals of Neurology, 55(2):207-212, (2004).

Minakawa, T., et al., "In Vitro Interaction of Astrocytes and Pericytes with Capillary-Like Structures of Brain Microvessel Endothelium," Laboratory Investigation, 65(1):32-40, (1991).

Murphy, J.R., et al., "Genetic Construction, Expression, and Melanoma-Selective Cytotoxicity of a Diphtheria Toxin-Related α-Melanocyte-Stimulating Hormone Fusion Protein," Proc. Natl. Acad. Sci. USA, 83:8258-8262, (1986).

Nadjar, A., et al., "Nuclear Factor κB Nuclear Translocation as a Crucial Marker of Brain Response to Interleukin-1. A Study in Rat and Interleukin-1 Type I Deficient Mouse," Journal of Neurochemistry, 87:1024-1036, (2003).

Nagai, N., et al., "Role of Plasminogen System Components in Focal Cerebral Ischemic Infarction: A Gene Targeting and Gene Transfer Study in Mice," Circulation, 99:2440-2444, (1999).

Nakayama, M., et al., "Multiple Pathways of TWEAK-Induced Cell Death," The Journal of Immunology, 168:734-743, (2002).

Nakayama, M., et al., "Fibroblast Growth Factor-Inducible 14 Mediated Multiple Pathways of TWEAK-Induced Cell Death," The Journal of Immunology, 170:341-348, (2003).

Namura, S., et al., "Activation and Cleavage of Caspase-3 in Apoptosis Induced by Experimental Cerebral Ischemia," The Journal of Neuroscience, 18(10):3659-3668, (1998).

Nedergaard, M., et al., "Focal Ischemia of the Rat Brain: Autoradiographic Determination of Cerebral Glucose Utilization, Glucose Content, and Blood Flow," Journal of Cerebral Blood Flow and Metabolism, 6(4):414-424, (1986).

Olsen, N.J., et al., "New Drugs for Rheumatoid Arthritis," The New England Journal of Medicine, 350(21):2167-2179, (2004).

Pantoni, L., et al., "Cytokines and Cell Adhesion Molecules in Cerebral Ischemia:Experimental Bases and Therapeutic Perspectives," Arteriosclerosis, Thrombosis, and Vascular Biology, 18:503-513, (1998).

Philip, R., et al., "Efficient and Sustained Gene Expression in Primary T Lymphocytes and Primary and Cultured Tumor Cells Mediated by Adeno-Associated Virus Plasmid DNA Complexed to Cationic Liposomes," Molecular and Cellular Biology, 14(4):2411-2418, (1994).

Plank, C., et al., "Gene Transfer into Hepatocytes Using Asialoglycoprotein Receptor Mediated Endocytosis of DNA Complexed with an Artificial Tetra-Antennary Galactose Ligand," Bioconjugate Chem., 3:533-539, (1992).

Potrovita, I., et al., "Tumor Necrosis Factor-Like Weak Inducer of Apoptosis-Induced Neurodegeneration," The Journal of Neuroscience, 24(38):8237-8244, (2004).

Romanic, A.M., et al., "Extracellular Matrix-Degrading Proteinases in the Nervous System," Brain Pathology, 4:145-156, (1994).

Rothwell, N., et al., "The Role of Interleukin 1 in Acute Neurodegeneration and Stoke: Pathophysiological and Therapeutic Implications," J. Clin. Invest., 100(11):2648-2652, (1997).
Ruan, Y.W., et al., "Apoptosis in the Adult Striatum After Transient Forebrain Ischemia and the Effects of Ischemic Severity," Brain Research, 982:228-240, (2003).
Saitoh, T. et al., "TWEAK Induces NF-κB2 p100 Processing and Long Lasting NF-κB Activation," The Journal of Biological Chemistry, 278(38):36005-36012, (2003).
Schneider, A., et al., "NF-κB is Activated and Promotes Cell Death in Focal Cerebral Ischemia," Nature Medicine, 5 (5):554-559, (1999).
Schroeter, M., et al., "Phagocytic Response in Photochemically Induced Infarction of Rat Cerebral Cortex," Stroke, 28 (2):382-386, (1997).
Stewart, P.A., et al., "Developing Nervous Tissue Induces Formation of Blood-Brain Barrier Characteristics in Invading Endothelial Cells: A Study Using Quail-Chick Transplantation Chimeras," Developmental Biology, 84:183-192, (1981).
Stoll, G., et al., "Inflammation and Glial Responses in Ischemic Brain Lesions," Progress in Neurobiology, 56:149-171, (1998).
Tanabe, K., et al., "Fibroblast Growth Factor-Inducible-14 is Induced in Axotomized Neurons and Promotes Neurite Outgrowth," The Journal of Neuroscience, 23(29):9675-9686, (2003).
Tran, N.D., et al., "Regulation of Brain Capillary Endothelial Thrombomodulin mRNA Expression," Stroke, 27:2304-2311, (1996).
Tran, N.D., et al., "Astrocyte Regulation of Endothelial Tissue Plasminogen Activator in a Blood-Brain Barrier Model," Journal of Cerebral Blood Flow and Metabolism, 18:1316-1324, (1998).
Trendelenburg, G., et al., "Serial Analysis of Gene Expression Identifies Metallothionein-II as Major Neuroprotective Gene in Mouse Focal Cerebral Ischemia," The Journal of Neuroscience, 22(14):5879-5888, (2002).
Wiley, S.R., et al., "TWEAK, A Member of the TNF Superfamily, is a Multifunctional Cytokine that Binds the TweakR/Fn14 Receptor," Cytokine & Growth Factor Reviews, 14:241-249, (2003).
Wiley, S.R., et al., "A Novel TNF Receptor Family Member Binds TWEAK and is Implicated in Angiogenesis," Immunity, 15:837-846, (2001).
Woffendin, C., et al., "Nonviral and Viral Delivery of a Human Immunodeficiency Virus Protective Gene into Primary Human T Cells," Proc. Natl. Acad. Sci. USA, 91:11581-11585, (1994).
Wu., C., et al., "Targeting Genes: Delivery and Persistent Expression of a Foreign Gene Driven by Mammalian Regulatory Elements in Vivo," The Journal of Biological Chemistry, 264(29):16985-16987, (1989).
Wu, G., et al., "Receptor-Mediated in Vitro Gene Transformation by a Soluble DNA Carrier System," The Journal of Biological Chemistry, 262(10):4429-4432, (1987).
Xu, L, et al., "Recombinant Adenoviral Expression of Dominant Negative IκBα Protects Brain from Cerebral Ischemic Injury," Biochemical and Biophysical Research Communications, 299:14-17, (2002).
Yepes, M., et al., "Tissue-Type Plasminogen Activator Induces Opening of the Blood-Brain Barrier Via the LDL Receptor-Related Protein," The Journal of Clinical Investigation, 112(10):1533-1540, (2003).
Yepes, M., et al., "Neuroserpin Reduces Cerebral Infarct Volume and Protects Neurons from Ischemia-Induced Apoptosis," Blood, 96(2):569-576, (2000).
Zhang, Z., et al., "A Mouse Model of Embolic Focal Cerebral Ischemia," Journal of Cerebral Blood Flow and Metabolism, 17(10):1081-1088, (1997).
Zhang, Z., et al., "Temporal Profile of Microglial Response Following Transient (2 h) Middle Cerebral Artery Occlusion," Brain Research, 744:189-198, (1997).
Zhang, Z., et al., "Adjuvant Treatment with Neuroserpin Increases the Therapeutic Window for Tissue-Type Plasminogen Activator Administration in a Rat Model of Embolic Stroke," Circulation, 106:740-745, (2002).
"Tissue Plasminogen Activator for Acute Ischemic Stroke," The National Institute of Neurological Disorders and Stroke rt-PA Stroke Study Group, N. Engl. J. Med., 333(24):1581-1587, (1995).
European Search Report issued in European Application No. EP 05848068.2, mailed Jun. 18, 2009.
I. Potrovita et al., "TWEAK—A Regulator of Neuronal Cell Death", Naunyn-Schmiedeberg's Archives of Pharmacology, Springer, Berlin, DE, vol. 369, No. Suppl. 01, p. R12, Mar. 9, 2004, XP009045913.
Manuel Yepes et al., "A Soluble Fn 14-Fc Decoy Receptor Reduces Infarct Volume in a Murine Model of Cerebral Ischemia", American Journal of Pathology, vol. 166, No. 2, pp. 511-520, Feb. 2005.
Chicheportiche, Y, et al., "Proinflammatory Activity of TWEAK on Human Dermal Fibroblasts and Synoviocytes: Blocking and Enhancing Effects of Anti-TWEAK Monoclonal Antibodies," Arthritis Research, 2002, vol. 4, pp. 126-133.
Nakayama, M., et al., "Fibroblast Growth Factor-Inducible 14 Mediates Multiple Pathways of TWEAK—Induced Cell Death" The Journal of Immunology, 2003, 170, pp. 341-348.
Nakayama, M., et al., "Involvement of TWEAK in interferon—stimulated Monocyte Cytotoxicity," J. Exp. Med., Nov. 6, 2000, vol. 192, No. 9, pp. 1373-1379.

* cited by examiner

|   | 1 | 2 | 3 | 4 | 5 | 6 | 7 | 8 |
|---|---|---|---|---|---|---|---|---|
| A | • | • | • | • | • | • | • | • |
| B | • | • | • | • | • | • | • |   |

SEQUENCE LISTING

<160> NUMBER OF SEQ ID NOS: 5

<210> SEQ ID NO 1
<211> LENGTH: 44
<212> TYPE: PRT
<213> ORGANISM: Mus musculus

<400> SEQUENCE: 1

Ala Pro Gly Thr Ser Pro Cys Ser Ser Gly Ser Ser Trp Ser Ala Asp
 1               5                  10                  15

Leu Asp Lys Cys Met Asp Cys Ala Ser Cys Pro Ala Arg Pro His Ser
             20                  25                  30

Asp Phe Cys Leu Gly Cys Ala Ala Ala Pro Pro Ala
         35                  40

<210> SEQ ID NO 2
<211> LENGTH: 240
<212> TYPE: PRT
<213> ORGANISM: Mus musculus

<400> SEQUENCE: 2

Leu Glu Ser Ser Thr Lys Val Asp Lys Lys Ile Val Pro Arg Asp Cys
 1               5                  10                  15

Gly Cys Lys Pro Cys Ile Cys Thr Val Pro Glu Val Ser Ser Val Phe
             20                  25                  30

Ile Phe Pro Pro Lys Pro Lys Asp Val Leu Thr Ile Thr Leu Thr Pro
         35                  40                  45

Lys Val Thr Cys Val Val Val Asp Ile Ser Lys Asp Asp Pro Glu Val
     50                  55                  60

Gln Phe Ser Trp Phe Val Asp Asp Val Glu Val His Thr Ala Gln Thr
 65                  70                  75                  80

Gln Pro Arg Glu Glu Gln Phe Asn Ser Thr Phe Arg Ser Val Ser Glu
                 85                  90                  95

Leu Pro Ile Met His Gln Asp Trp Leu Asn Gly Lys Glu Phe Lys Cys
            100                 105                 110

Arg Val Asn Ser Ala Ala Phe Pro Ala Pro Ile Glu Lys Thr Ile Ser
        115                 120                 125

Lys Thr Lys Gly Arg Pro Lys Ala Pro Gln Val Tyr Thr Ile Pro Pro
    130                 135                 140

Pro Lys Glu Gln Met Ala Lys Asp Lys Val Ser Leu Thr Cys Met Ile
145                 150                 155                 160

Thr Asp Phe Phe Pro Glu Asp Ile Thr Val Glu Trp Gln Trp Asn Gly
                165                 170                 175

```
Gln Pro Ala Glu Asn Tyr Lys Asn Thr Gln Pro Ile Met Asp Thr Asp
            180                 185                 190

Gly Ser Tyr Phe Val Tyr Ser Lys Leu Asn Val Gln Lys Ser Asn Trp
            195                 200                 205

Glu Ala Gly Asn Thr Phe Thr Cys Ser Val Leu His Glu Gly Leu His
            210                 215                 220

Asn His His Thr Glu Lys Ser Leu Ser His Ser Pro Gly Phe Gly Pro
225                 230                 235                 240

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Gln Lys Leu Ile Ser Glu Glu Asp Leu
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 4

His His His His His His
1               5

<210> SEQ ID NO 5
<211> LENGTH: 334
<212> TYPE: PRT
<213> ORGANISM: Mus musculus

<400> SEQUENCE: 5

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Ala Pro Gly
            20                  25                  30

Thr Ser Pro Cys Ser Ser Gly Ser Ser Trp Ser Ala Asp Leu Asp Lys
            35                  40                  45

Cys Met Asp Cys Ala Ser Cys Pro Ala Arg Pro His Ser Asp Phe Cys
        50                  55                  60

Leu Gly Cys Ala Ala Ala Pro Pro Ala Leu Glu Ser Ser Thr Lys Val
65                  70                  75                  80

Asp Lys Lys Ile Val Pro Arg Asp Cys Gly Cys Lys Pro Cys Ile Cys
                85                  90                  95

Thr Val Pro Glu Val Ser Ser Val Phe Ile Phe Pro Pro Lys Pro Lys
            100                 105                 110

Asp Val Leu Thr Ile Thr Leu Thr Pro Lys Val Thr Cys Val Val Val
            115                 120                 125

Asp Ile Ser Lys Asp Asp Pro Glu Val Gln Phe Ser Trp Phe Val Asp
        130                 135                 140

Asp Val Glu Val His Thr Ala Gln Thr Gln Pro Arg Glu Glu Gln Phe
145                 150                 155                 160

Asn Ser Thr Phe Arg Ser Val Ser Glu Leu Pro Ile Met His Gln Asp
```

-continued

```
                165                 170                 175
Trp Leu Asn Gly Lys Glu Phe Lys Cys Arg Val Asn Ser Ala Ala Phe
            180                 185                 190

Pro Ala Pro Ile Glu Lys Thr Ile Ser Lys Thr Lys Gly Arg Pro Lys
            195                 200                 205

Ala Pro Gln Val Tyr Thr Ile Pro Pro Lys Glu Gln Met Ala Lys
            210                 215                 220

Asp Lys Val Ser Leu Thr Cys Met Ile Thr Asp Phe Phe Pro Glu Asp
225                 230                 235                 240

Ile Thr Val Glu Trp Gln Trp Asn Gly Gln Pro Ala Glu Asn Tyr Lys
            245                 250                 255

Asn Thr Gln Pro Ile Met Asp Thr Asp Gly Ser Tyr Phe Val Tyr Ser
            260                 265                 270

Lys Leu Asn Val Gln Lys Ser Asn Trp Glu Ala Gly Asn Thr Phe Thr
            275                 280                 285

Cys Ser Val Leu His Glu Gly Leu His Asn His His Thr Glu Lys Ser
    290                 295                 300

Leu Ser His Ser Pro Gly Phe Gly Pro Glu Gln Lys Leu Ile Ser Glu
305                 310                 315                 320

Glu Asp Leu Asn Ser Ala Val Asp His His His His His His
                325                 330
```

TWEAK AS A THERAPEUTIC TARGET FOR TREATING CENTRAL NERVOUS SYSTEM DISEASES ASSOCIATED WITH CEREBRAL EDEMA AND CELL DEATH

This application claims priority from U.S. Provisional Application 60/626,054, filed Nov. 8, 2004 and U.S. Provisional Application 60/636,024, filed Dec. 13, 2004, the entire contents of which are incorporated herein by reference.

This invention was made with government support under Grant Nos. NS02223, NS49478, HL55374, HL55747 and HL39727 awarded by the Department of Health and Human Services, National Institutes of Health. The U.S. government has certain rights in the invention.

FIELD OF THE INVENTION

The disclosure generally relates to the field of Neurology. More particularly, it relates to compositions and methods for treat neurological diseases associated with an increase in the permeability of the blood brain barrier (BBB), cerebral edema and/or cell death.

BACKGROUND OF THE TECHNOLOGY

Stroke is the second leading cause of death and a major cause of disability in the world. This clinical syndrome is characterized by rapidly developing symptoms and/or signs of focal or global loss of cerebral function with no apparent cause other than that of vascular origin. Blood brain barrier (BBB) breakdown and brain (cerebral) edema with subsequent increase in intracranial presume is the major cause of death in stroke patients. The BBB consists of endothelial cells, pericytes, astrocytes, and the vascular basement membrane. Its main function is to form a tight barrier that regulates the entry of selected molecules from the blood into the central nervous system (CNS), and to prevent the passage of potentially harmful substances into the brain. The regulation of BBB permeability is a necessary part of normal physiology; however, as mentioned above in pathologic situations such as acute cerebral ischemia, excessive increases in vascular permeability lead to opening of the BBB and vasogenic edema (Garcia J. H. et al., *Acta Neuropathol.* (Berl) 43:85-95 (1978), and Baker, R. N et al., *J. Neuropathol. Exp. Neurol.* 30:668-679 (1971)).

Tumor necrosis factor-like weak inducer of apoptosis (TWEAK) is a member of the tumor necrosis factor (TNF) superfamily of cytokines. TWEAK is initially synthesized as a type II transmembrane protein but can be cleaved to generate a 17-kDa soluble factor with biological activity (see FIG. 1 and Chicheportiche, Y. et al, *J. Biol. Chem.* 272:32401-32410 (1997)). Soluble TWEAK induces various cellular responses when it is added to cells in culture. TWEAK activity is mediated via binding to fibroblast growth factor-inducible 14 (Fn14), a member of the TNF receptor superfamily (see. e.g., Wiley, S. R. et al., *Cytokine Growth Factor Rev.* 14:241-249 (2003)). The Fn14 gene is expressed in a variety of cell and tissue types (supra). In addition, Fn14 gene expression is up-regulated following growth factor stimulation of quiescent cell cultures and after injury to the blood vessel wall or the liver (Wiley, S. R. et al., *Immunity* 15:837-846 (2001); Feng, S. L. et al., *Am. J. Pathol.* 156:1253-1261(2000)).

It has been shown that TWEAK binding to Fn14 activates the NF-κB (see e.g., Brown, S. A. et al., *Biochem. J.* 371:395-403 (2003)), extracellular signal-regulated kinase (ERK) and c-Jun NH2-terminal kinase (JNK) signal transduction pathways (see e.g. FIG. 2 and Donohue, P. J. et al., *Arterioscler. Thromb. Vasc. Biol.,* 23:594-600 (2003).

The neurovascular unit (NVU) is a dynamic structure consisting of endothelial cells, the basal lamina, the astrocytic foot processes, the pericyte and the neuron. During cerebral ischemia, disruption of the NVU results in the development of cerebral edema (Baker R. N. et al., *J. Neuropathol. Exp. Neurol.* 30:668-679, (1971)). NF-κB is expressed at low levels in the CNS (Kaltschmidt C. et al., *Mol. Cell Biol.* 14:3981-3992 (1994)). It has been reported that NF-κB activity is significantly increased in animal models of ischemic stoke and data obtained from mice deficient in the NF-κB p50 subunit indicates that NF-κB activation enhances ischemic neuronal death (Schneider, A. et al., *Nat. Med.* 5:554-559 (1999)). NF-κB signaling and NF-κB-inducible gene products have been implicated in increased BBB permeability and cell death during cerebral ischemia (Xu, L. et al., *Biochem. Biophys. Res. Commun.* 299:14-17 (2002); Nadjar A. et al., *J. Neurochem.* 87:1024-1036(2003)).

Several TWEAK-inducible genes, such as IL-8, IL-6, MCP-1, GM-CSF, MMP-9, ICAM-1 and RANTES, are known to be regulated via the NF-κB pathway (see e.g., Lynch, C. N. et al., *J. Biol. Chem.* 274:8455-8459 (1999); Kim, S. H. et al., *Circ. J.* 68:396-3991 (2004); Jin, L. et al., *J. Invest. Dermatol.* 122:1175-1179 (2004); Mattson, M. P. and Carnandola, S. *J. Clin. Invest.* 107:247-254 (2001). It has been demonstrated that IL-6 and MMP-9 play a central role in the development of cerebral edema and the increase of permeability of the BBB, respectively (Pantoni, L. et al., *Arterioscler. Thromb. Vasc. Biol.* 18:503-513 (1998); Romanic, A. M. and Madri, J. A., *Brain Pathol.* 4:145-156 (1994)). It has also been reported that inhibition of IL-1 and IL-8 during cerebral ischemia results in a significant decrease in cerebral edema (see e.g., Rothwell, N, et al., *J. Clin. Invest.* 100:2648-2652 (1997); Matsumoto, T. et al., *Lab. Invest.* 77:119-125 (1997)).

In summary, disruption of the BBB with vasogenic edema is the most common cause of neurological deterioration and death following acute stoke. Although the use of tPA has been approved by the FDA for thrombolysis in patients with acute stroke, only a limited number of patients seem to benefit from this form of treatment (The National Institute of Neurological Disorders and Stroke t-PA Stroke Study Group, *N. Engl. J. Med.* 333:1581-1587 (1995)). Therefore, there remains a long-felt need in the art for identification of new therapeutic molecules that ameliorate cerebral ischemia-induced BBB breakdown and subsequent cell death and serve as new therapeutic agents for patients suffering from stroke and/or cerebral edema.

SUMMARY

One aspect of the present invention relates to a method for treating a condition associated with an increase in blood brain barrier (BBB) permeability, the method comprising administering to a subject in need thereof an effective amount of an agent that either disrupts interaction between a TWEAK protein and a Fn14 receptor, or interferes a Fn14 signal transduction pathway, Fn14 expression, or TWEAK expression.

In one embodiment, the agent comprises an Fn14 decoy receptor. In another embodiment, the agent comprises an anti-TWEAK antibody or anti-Fn14 antibody. In yet another embodiment, the agent comprises an antisense polynucleotide or an RNAi molecule. In yet another embodiment; the method further comprises co-administering to the subject an inhibitor of a NF-κB-regulated biomolecule, such as MMP-9.

In yet another embodiment, the method further comprises co-administering to the subject a tissue plasminogen activator (tPA).

The methods of the present invention may be used to treat stroke and other diseases associated with increased BBB permeability, such as, for example, head trauma, seizures, meningitis, encephalitis, primary brain tumors, brain metastasis, brain abscesses, hemorrhagic stroke, septic encephalopathy, HIV-induced dementia, multiple sclerosis, and/or Alzheimer's disease.

TWEAK is a 249-amino acid type II transmembrane glycoprotein that can be proteolytically processed by the enzyme furin into a soluble 156-amino acid monomeric cytokine. The TWEAK receptor, Fn14, is a 129-amino acid type I transmembrane protein that is processed by signal peptidase into a mature 102-amino acid plasma membrane-anchored receptor.

Figure 1:
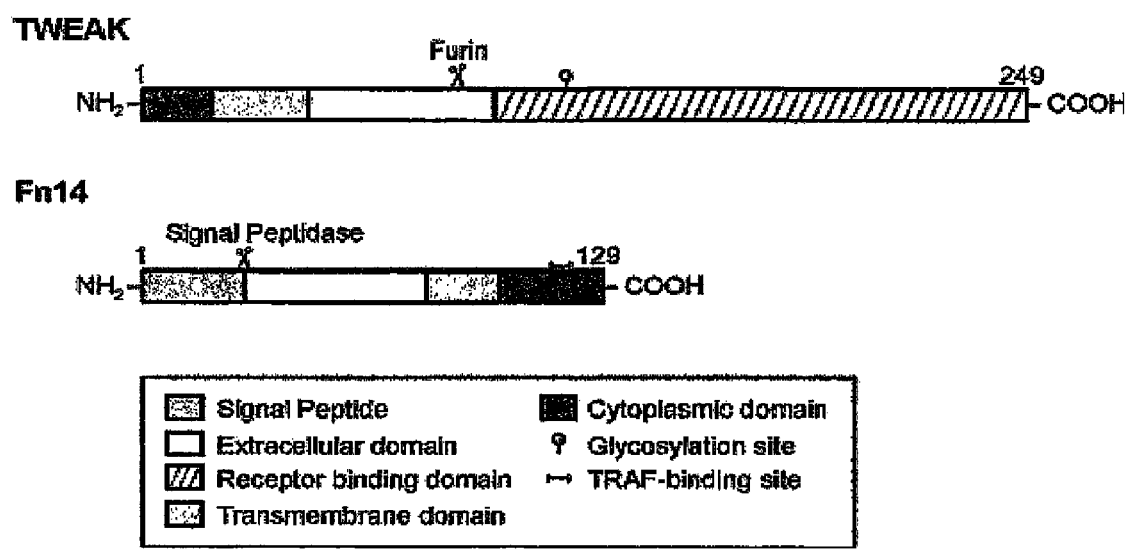
FIG. 1 is a diagram showing structural features of the TWEAK and Fn14 proteins.
Figure 2:
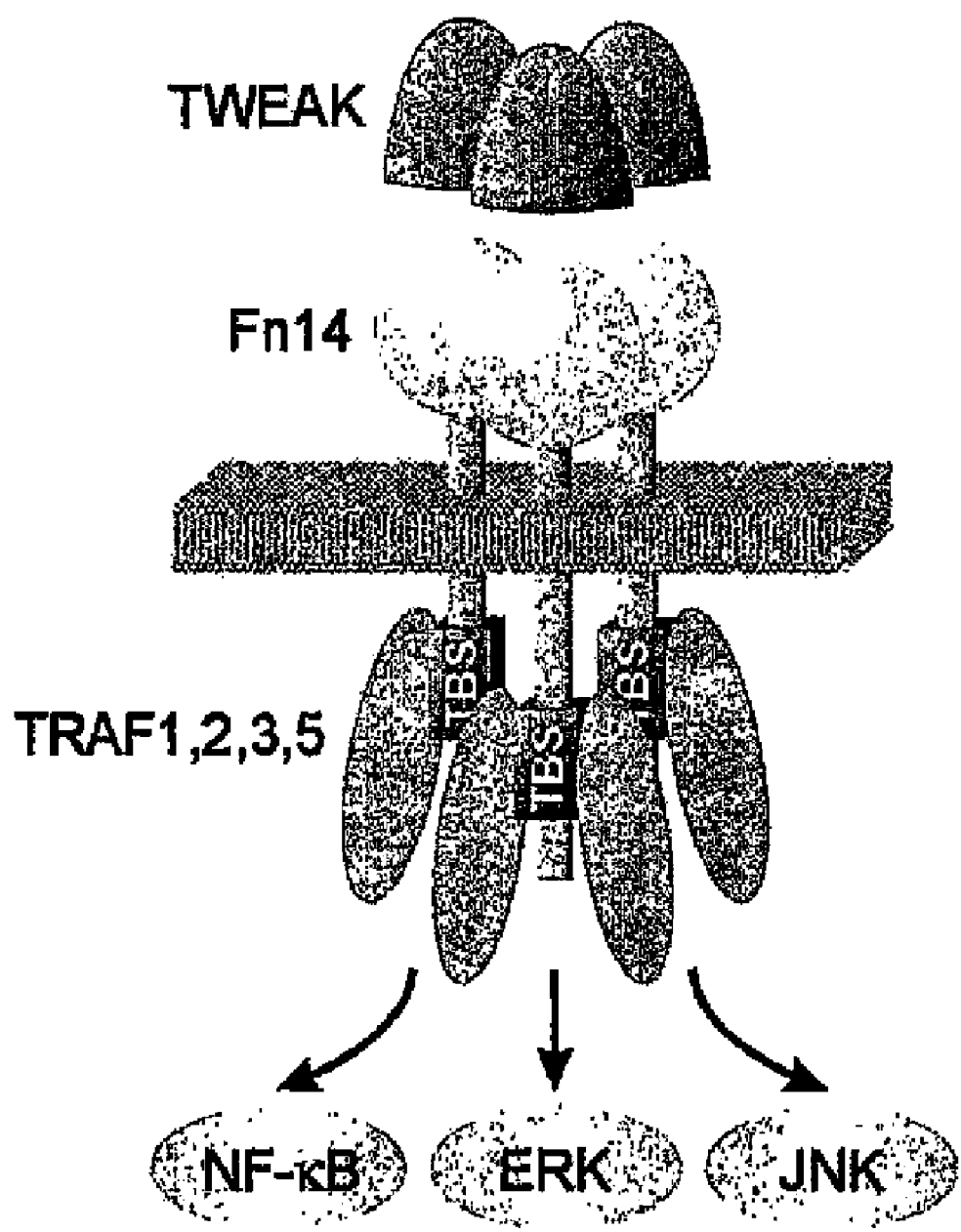

FIG. 2 is a schematic drawing showing the TWEAK-Fn14 signaling system.

Soluble TWEAK monomers associate into timers and then bind to cell surface Fn14 receptors. Receptor trimerization recruits TRAY adaptor proteins to the TRAP binding site (TBS) on the Fn14 cytoplasmic tail leading to signal transduction pathway activation and cellar responses.

Figure 3:
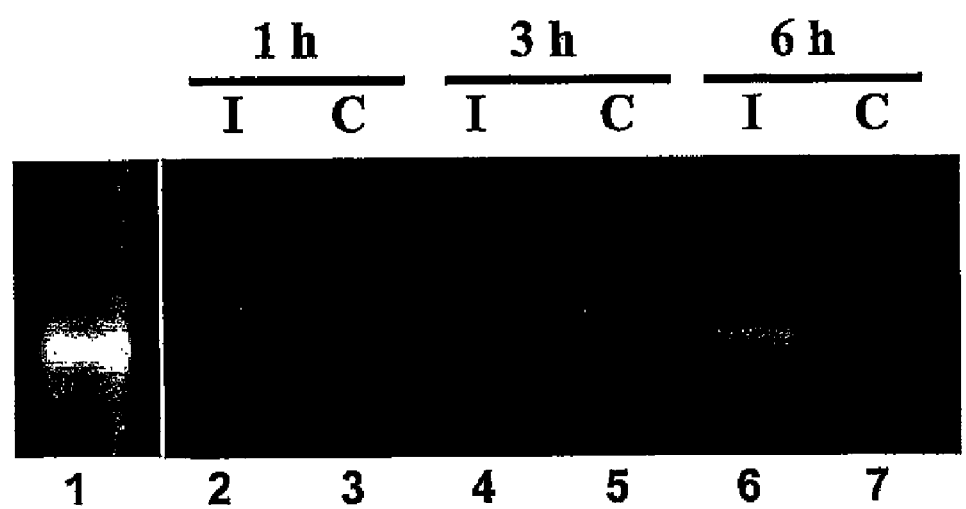

FIG. 3 shows MMP-9 activity in rat brain following cerebral ischemia.

Gelatin zymography assay of brain extracts from rats at 1 (lanes 2 & 3), 3 (lanes 4 & 5), and 6 hours (lanes 6 & 7) following MCAO. Lane 1 is purified human proMMP-9 and all other lanes are brain extracts. Lanes 2, 4 and 6 are ipsilateral to the ischemic area and lanes 3, 5 and 7 are contralateral.

Figure 4:
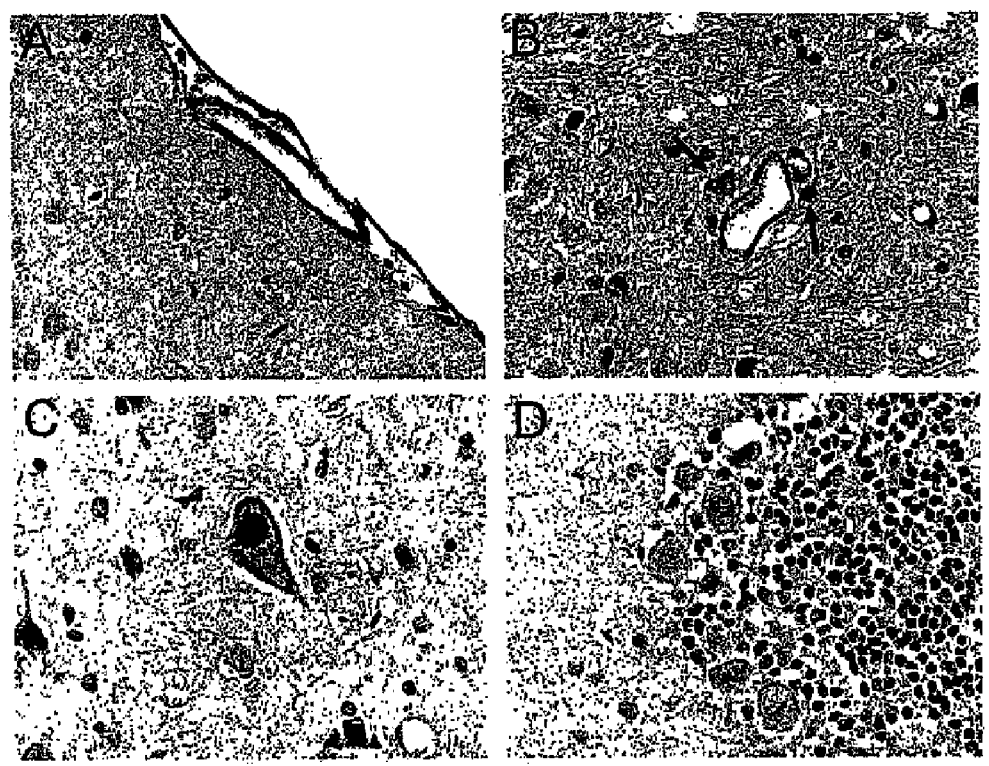

FIG. 4 shows immunohistochemical analysis of TWEAK and Fn14 expression in normal mouse brain.

Panels A-B show TWEAK staining in pial and intracerebral blood vessels surrounded by cells with morphological features of astrocytes (arrows). Panels C-D show Fn14 staining in cortical neurons and cerebellar Purkinje cells. Magnification ×40.

Figure 5:
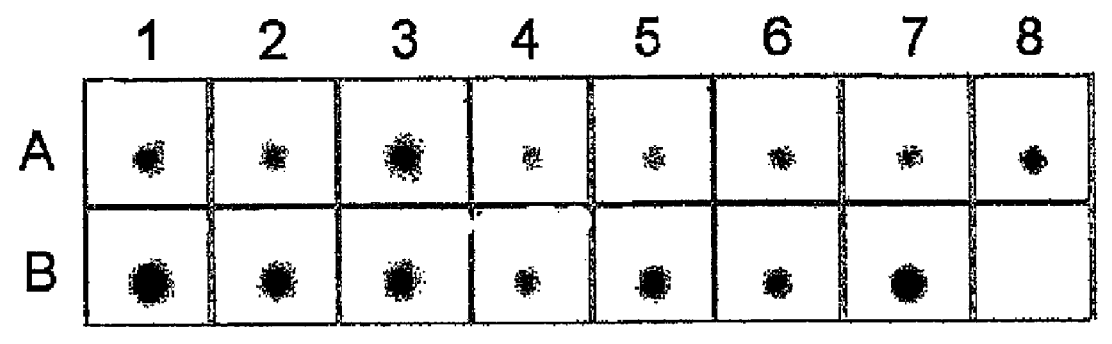

FIG. 5 shows Fn14 mRNA expression in human CNS specimens.

RNA dot blot containing normalized loading levels of poly (A)+RNA isolated from various tissues was hybridized to an Fn14 cDNA probe. Grid coordinates for tissue types are as follows: A1, whole brain; A2, amygdala; A3, caudate nucleus; A4, cerebellum; A5, cerebral cortex; A6, frontal lobe; A7, hippocampus; A8, medulla oblongata; B1, occipital lobe; B2, putamen; B3, substantia nigra; B4, temporal lobe; B5, thalamus; B6, subthalamic nucleus; B7, spinal cord.

Figure 6:
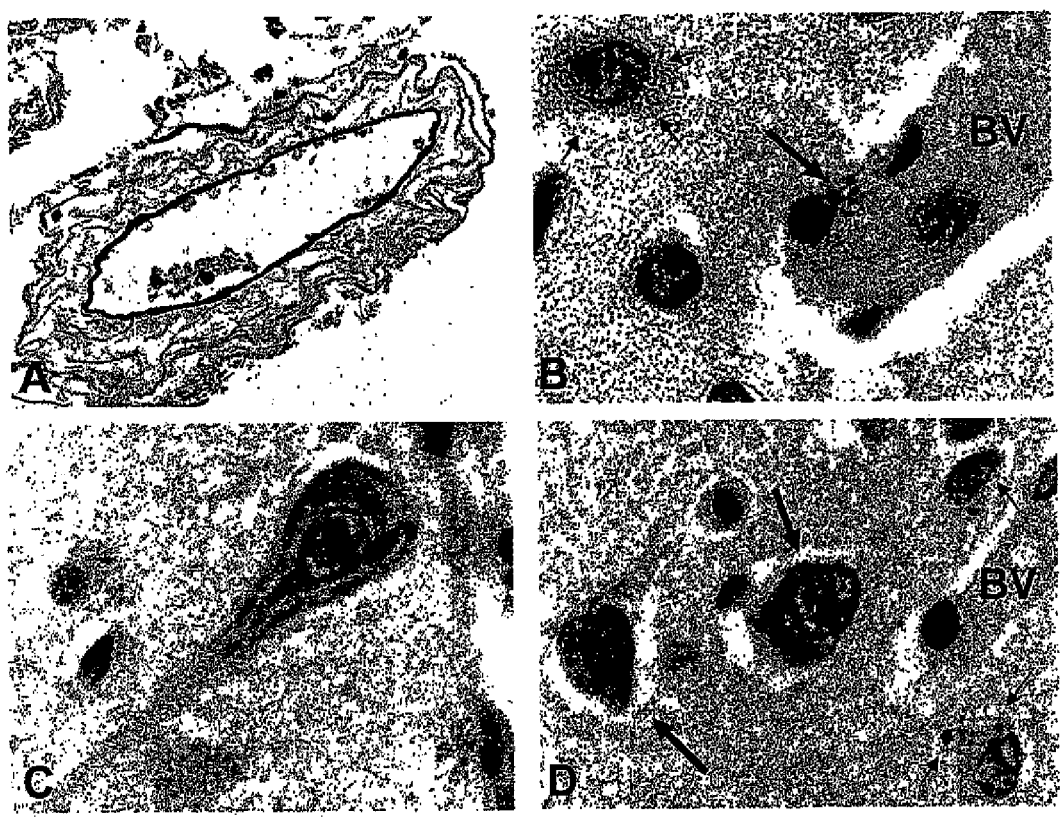

FIG. 6 shows immunohistochemical staining of TWEAK and Fn14 in a normal human brain.

Panel A shows TWEAK staining in endothelial cells of a blood vessel of medium caliber. Panel B shows TWEAK staining in astrocytes (thin arrows) and cells with morphological features of perivascular microglia (thick arrows) surrounding a blood vessel (BV). Panel C shows Fn14 staining in a cortical neuron. Panel D shows Fn14 staining in neurons (thick arrows) and cells with morphological features of perivascular microglia (thin arrows) surrounding a blood vessel (BV). Magnification in A is ×40, and in B,C,D is ×100.

Figure 7:
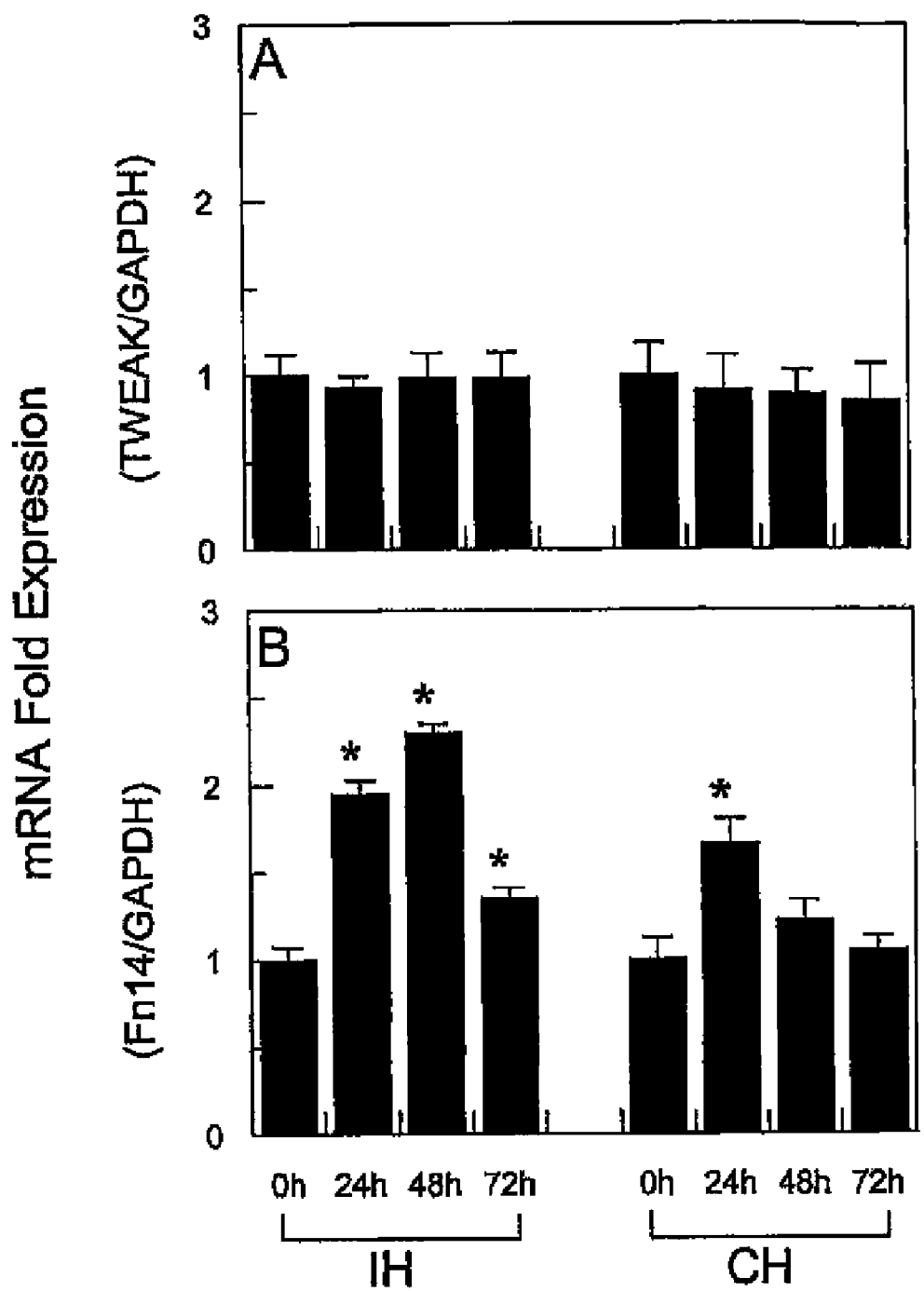

FIG. 7 shows real-time quantitative RT-PCR analysis of TWEAK and Fn14 mRNA expression in a mouse brain after cerebral infarction.

Mice were subjected to MCAO and then sacrificed at the indicated time points. RNA was isolated from the ipsilateral hemisphere (IH) and contralateral hemisphere (CH) regions dissected from the same brain specimen and real-time RT-PCR was performed to analyze TWEAK mRNA (panel A) or Fn14 mRNA (panel B) expression. TWEAK and Fn14 mRNA expression levels were normalized to GAPDH mRNA expression, and then the IH and CH 24, 48, and 72 hour values were normalized to the corresponding 0 hour value.

Figure 8:
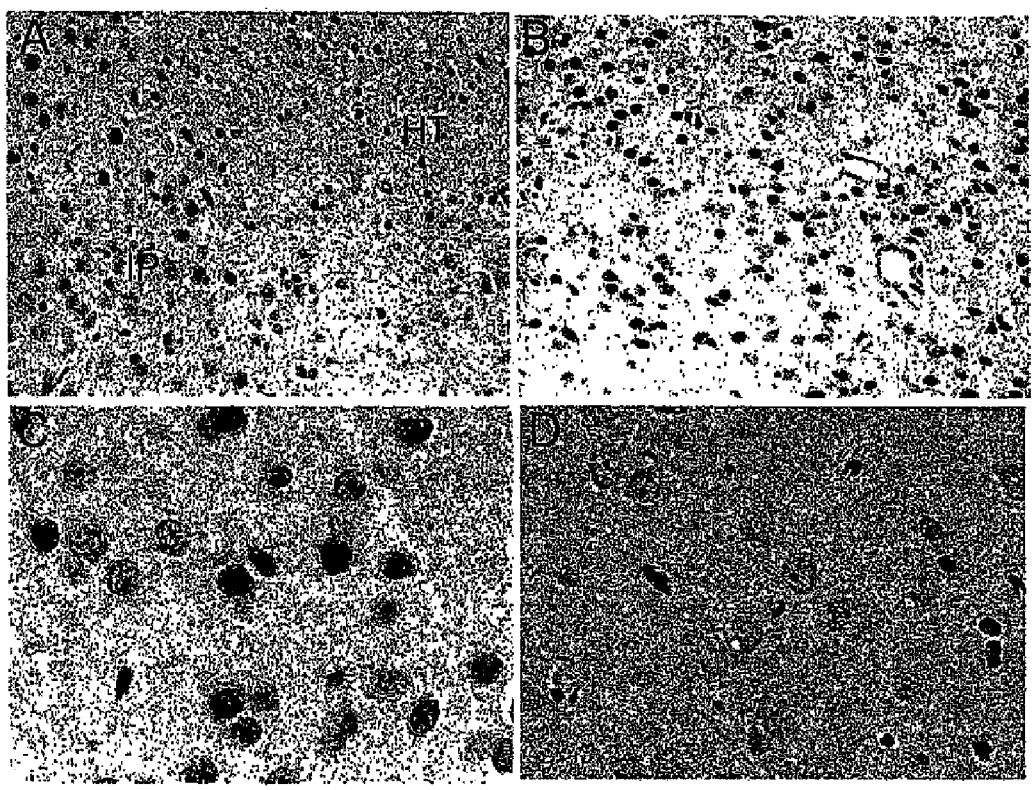

FIG. 8 shows immunohistochemical analysis of TWEAK expression in a mouse brain at 48 hours after cerebral infarction.

Mice were subjected to MCAO and sacrificed 48 hours later. Tissue sections were prepared from the area surrounding the necrotic core in the ipsilateral hemisphere (panels A and C) and from a corresponding area in the healthy, non-ischemic contralateral hemisphere (panels B and D) and stained with anti-TWEAK antibodies. Abbreviations: IP: ischemic penumbra, HT: healthy tissue. Magnification is 20× in A and B and 40× in C and D.

Figure 9:
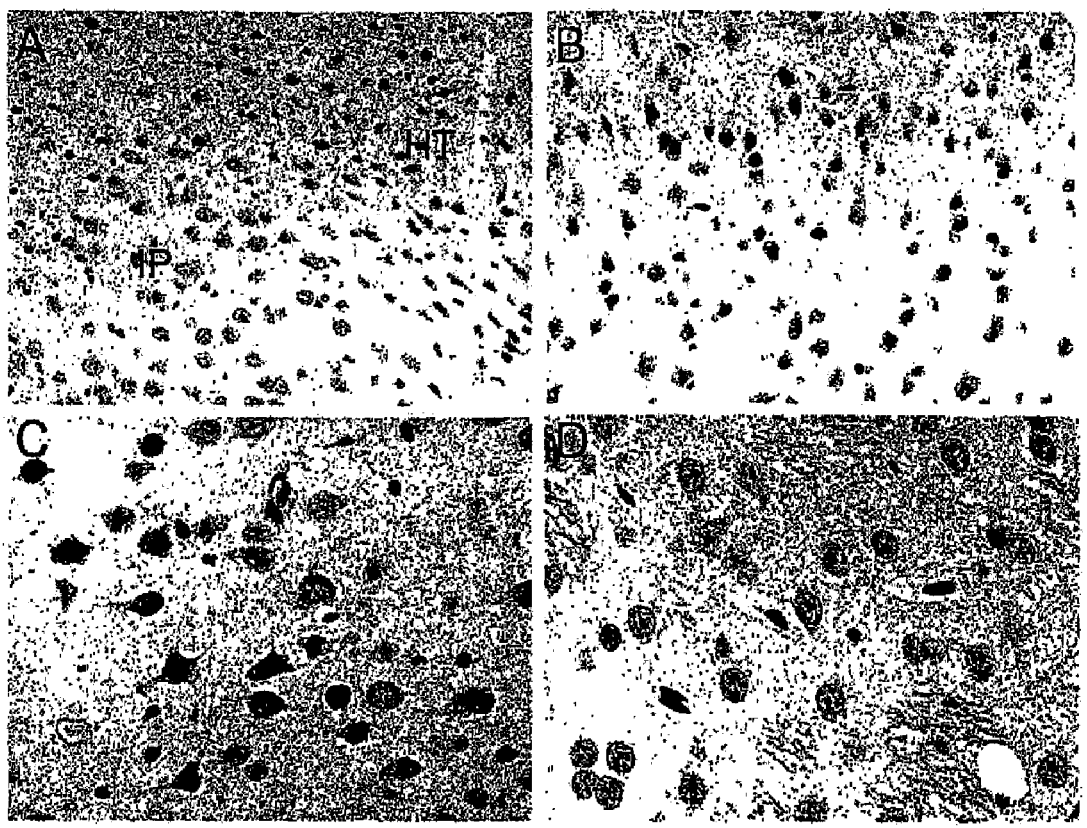

FIG. 9 shows immunohistochemical analysis of Fn14 expression in a mouse brain at 48 hours after cerebral infarction.

Mice were subjected to MCAO and sacrificed 48 hours later. Tissue sections were prepared from the area surrounding the necrotic core in the ipsilateral hemisphere (panels A and C) and from a corresponding area in the healthy, nonischemic contralateral hemisphere (panels B and D) and stained with anti-Fn14 antibodies. Abbreviations: IP: ischemic penumbra, HT: healthy tissue. Magnification is 20× in A and B and 40× in C and D.

Figure 10:
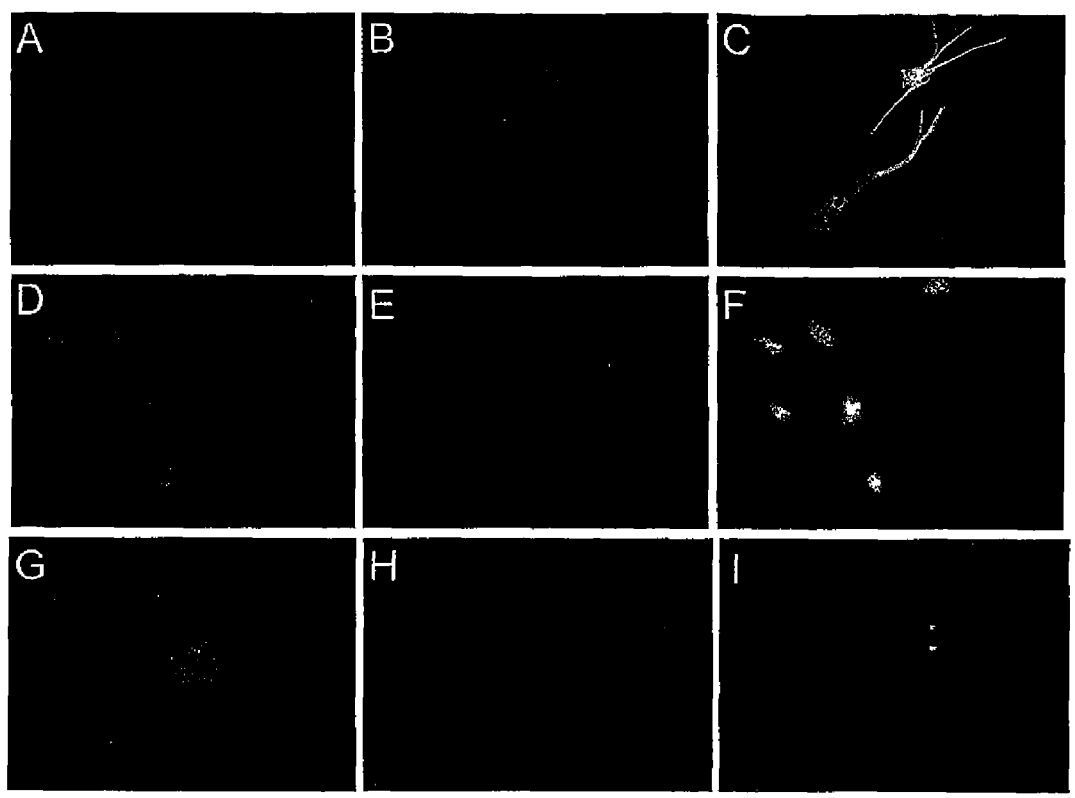

FIG. 10 shows indirect immunofluorescence analysis of TWEAK and Fn14 expression in mouse cerebral cortex-derived cell cultures.

Astrocyte enriched cell cultures were incubated with anti-TWEAK antibodies in combination with anti-GEAP antibodies. TWEAK staining is shown in panel A, GFAP staining is shown in panel B, and a merged image is shown in panel C. Neuron-enriched and microglial-enriched cell cultures were incubated with anti-Fn14 antibodies in combination with anti-NeuN or anti-Mac-1 antibodies. Fn14 staining is shown in panels D and G, NeuN staining is shown in panel E and Mac-1 in panel H; merged images are shown in panels F & I. Magnification is ×60 in Panels A-F and ×100 in Panels G-I.

Figure 11:
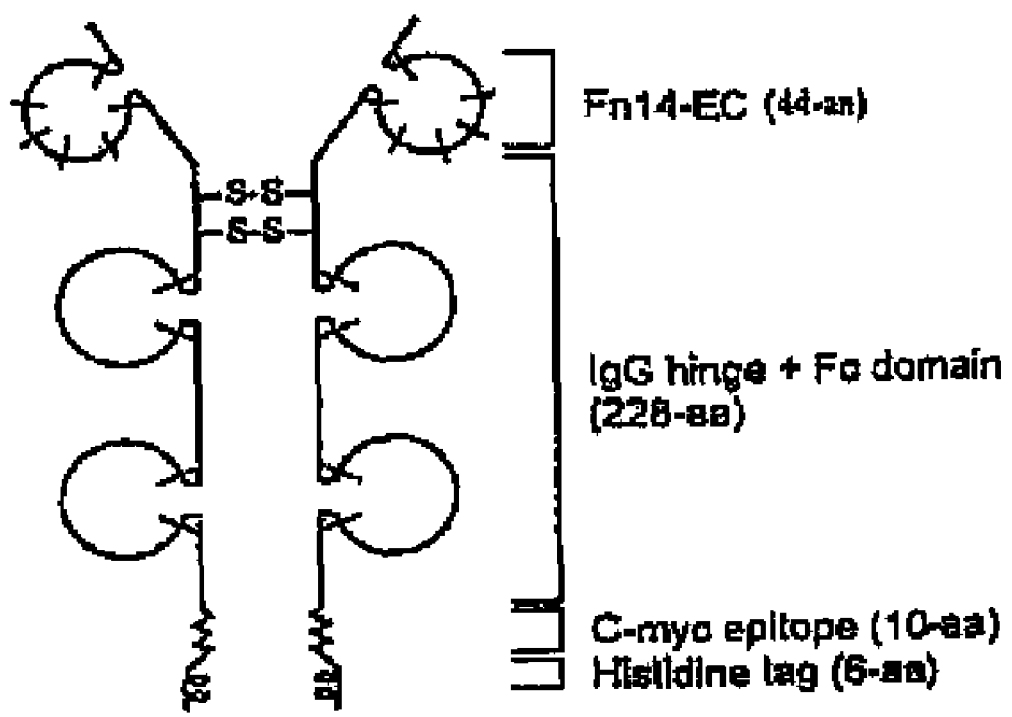

FIG. 11 shows structural properties of the murine Fn14-Fc fusion protein.

A schematic depiction of the Fn14-Fc decoy receptor is shown. The cysteine-rich domains are represented by loops and the bars represent cysteine residues.

Figure 12:
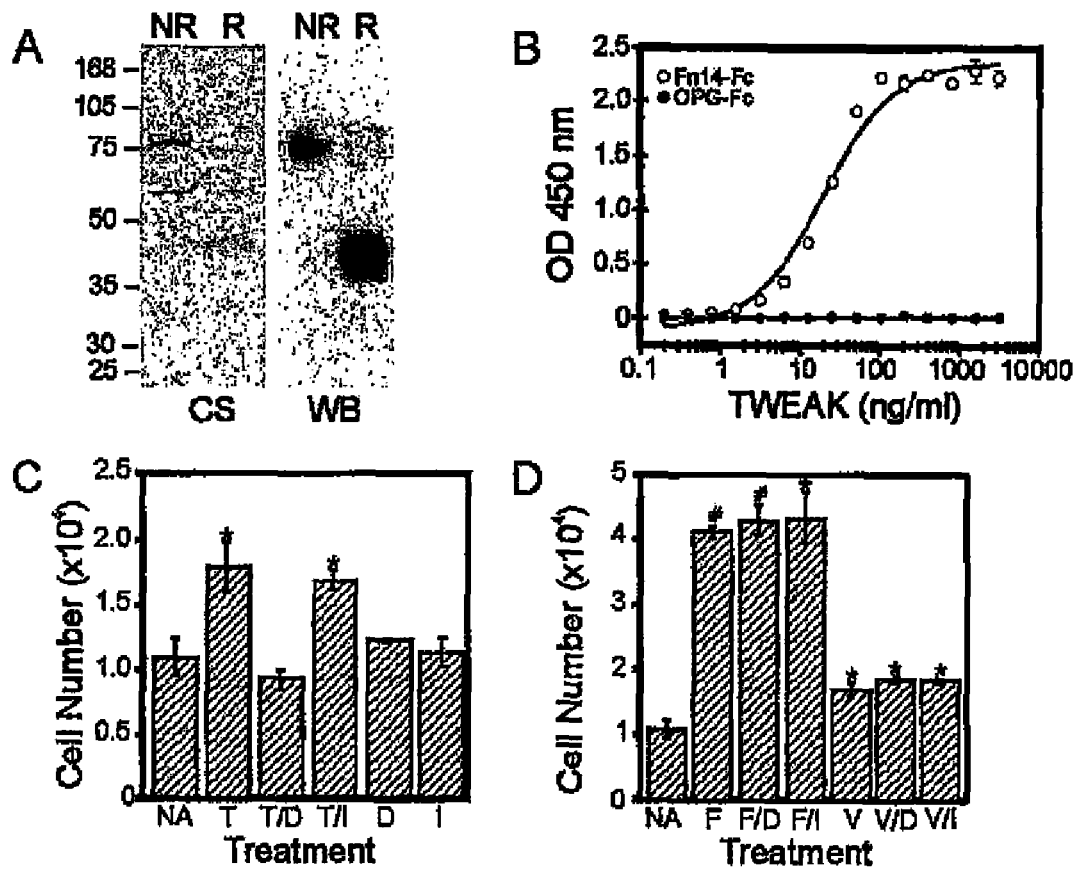

FIG. 12 shows effect of the Fn14-Fc decoy receptor on TWEAK-, FGF-2-, or VEGF-A-stimulated human endothelial cell (EC) proliferation.

A) Fn14-Fc protein purified from the conditioned medium of stably transfected human 293T cells was incubated with either nonreducing (NR) or reducing (R) gel loading buffer and then subjected to SDS PAGE. The samples were run in duplicate. One portion of the gel was stained with Coomassie Blue (CS; Coomassie-stained) and the other portion was transferred to nitrocellulose for subsequent Western blot analysis using anti-Fn14 antiserum (WB; Western blot). B) TWEAK binding to immobilized Fn14-Fc protein was quantified using an ELISA. OPG-Fc was used as a control for non-specific binding. C) EC were seeded at low density, placed into growth factor-reduced medium for one day and then either left unstimulated (NA; no addition) or stimulated with 50 ng/ml TWEAK (T), 2.5 ug/ml Fn14-Fc decoy receptor (D; decoy), or 2.5 ug/ml mouse IgG isotype control (I;

IgG) alone or in combinations for three days. D) EC were treated as above and then either left unstimulated (NA; no addition) or stimulated with 10 ng/ml FGF-2 (F), 30 ng/ml VEGF-A (V), 2.5 ug/ml Fn14-Fc decoy receptor (D), or 2.5 ug/ml mouse IgG control (I) alone or in combinations for three days.

Figure 13:
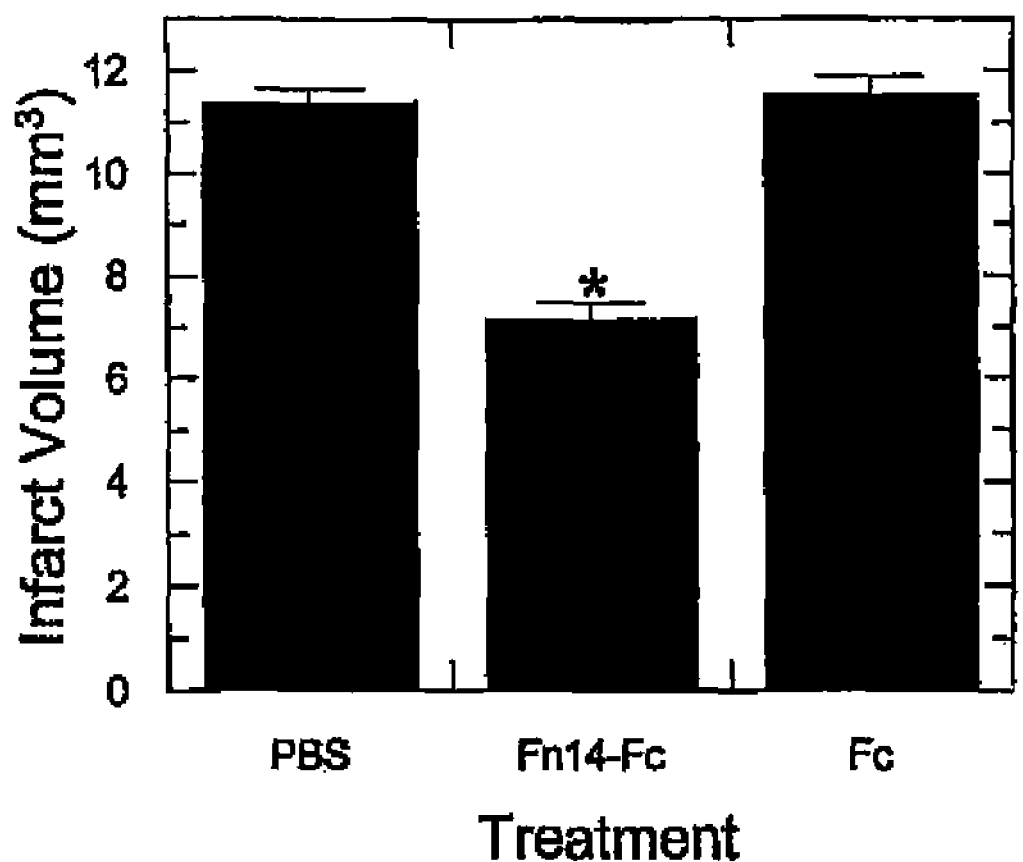

FIG. 13 shows the effect of Fn14-Fc or Fc administration on infarct volume.

Mice were subjected to MCAO and then vehicle (PBS), Fn14-Fc protein, or Fc protein was injected into the third ventricle. Mice were sacrificed 72 hours later and stroke volumes were measured. N=5 per group and the values shown are mean +/−SEM. *p<0.05 vs. animals injected with PBS or FP protein.

Figure 14:
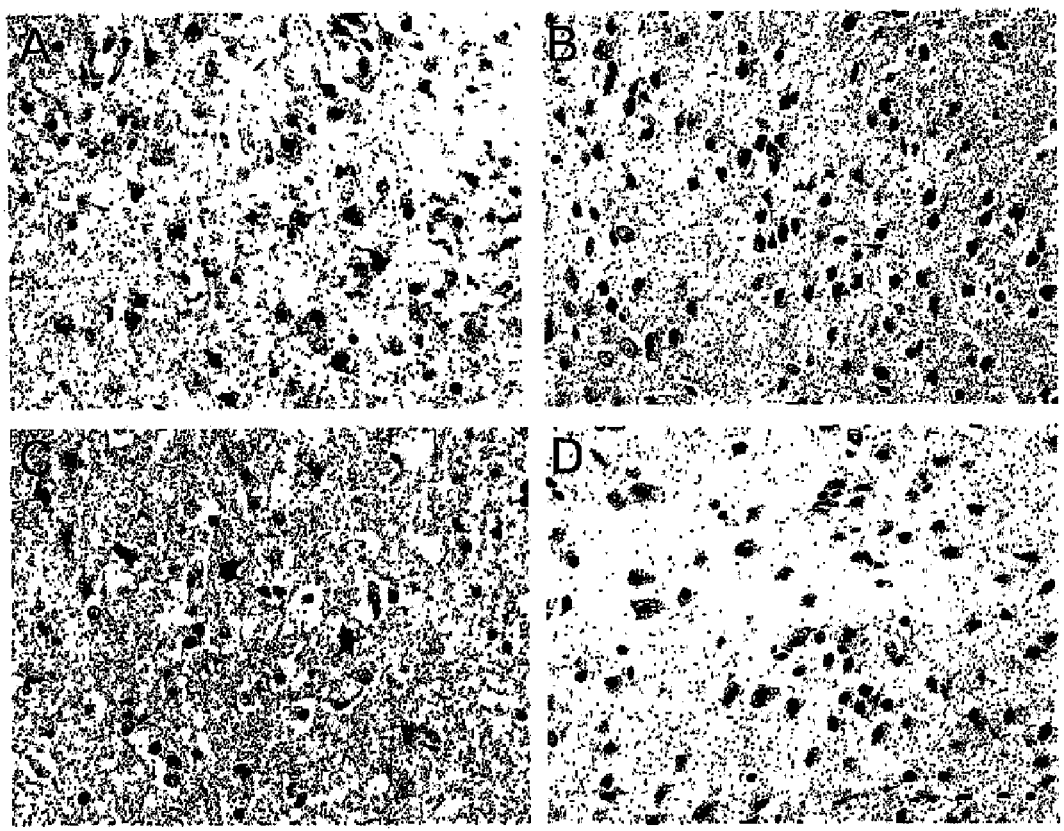

FIG. 14 shows the effect of Fn14-Fc administration on ischemia-induced microglial activation in the ischemic penumbra.

Mice were subjected to MCAO and treated with either PBS (panels A and B) or with the Fn14-Fc decoy receptor (panels C and D) and sacrificed 72 hours later. Tissue sections were prepared from the area surrounding the necrotic core in the ipsilateral hemisphere (panels A and C) and from a corresponding area in the healthy, nonischemic contralateral hemisphere (panels B and D) and stained with anti-Mac-1 antibodies. Magnification is 40×.

Figure 15:
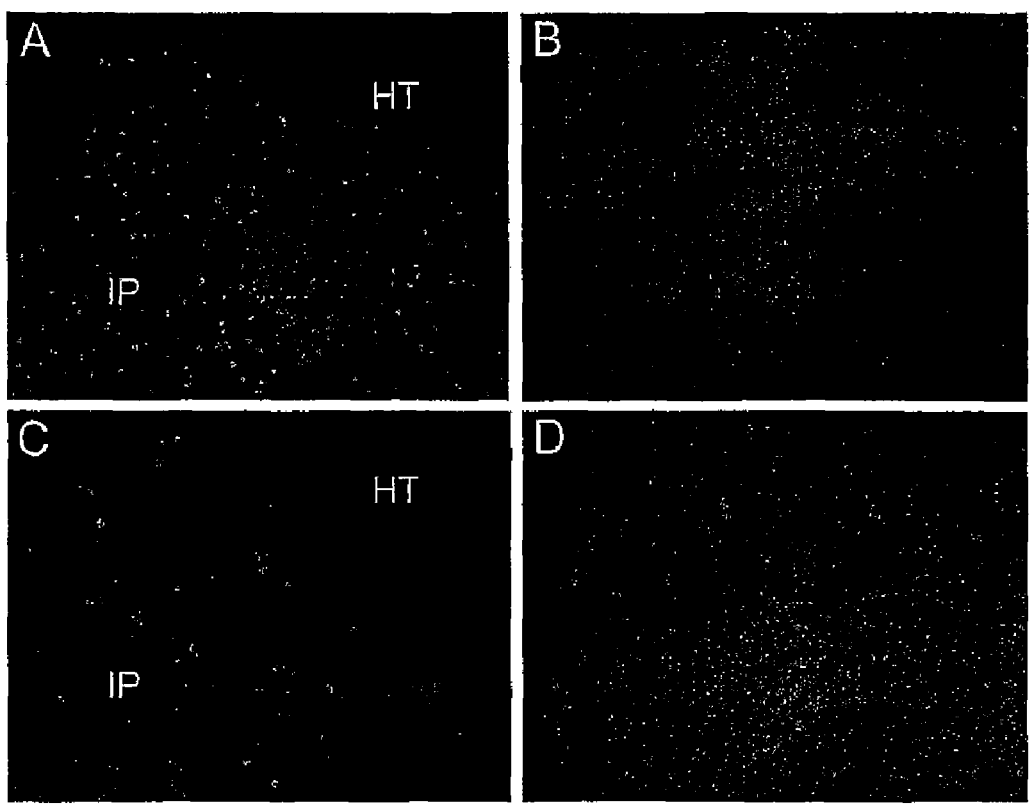

FIG. 15 shows the effect of Fn14-Fc administration on ischemia-induced apoptotic cell death in the ischemic penumbra.

Mice were subjected to MCAO and treated with either PBS (panels A and B) or with the Fn14-Fc decoy receptor (panels C and D) and sacrificed 72 hours later. Tissue sections were prepared from the area surrounding the necrotic core in the ipsilateral hemisphere (panels A and C) and from a corresponding area in the healthy, non-ischemic contralateral hemisphere panels B and D) and stained for apoptotic cells using a TUNEL-based fluorescence assay. Abbreviations: IP: ischemic penumbra, HT: healthy tissue. Magnification is 20×.

Figure 16:
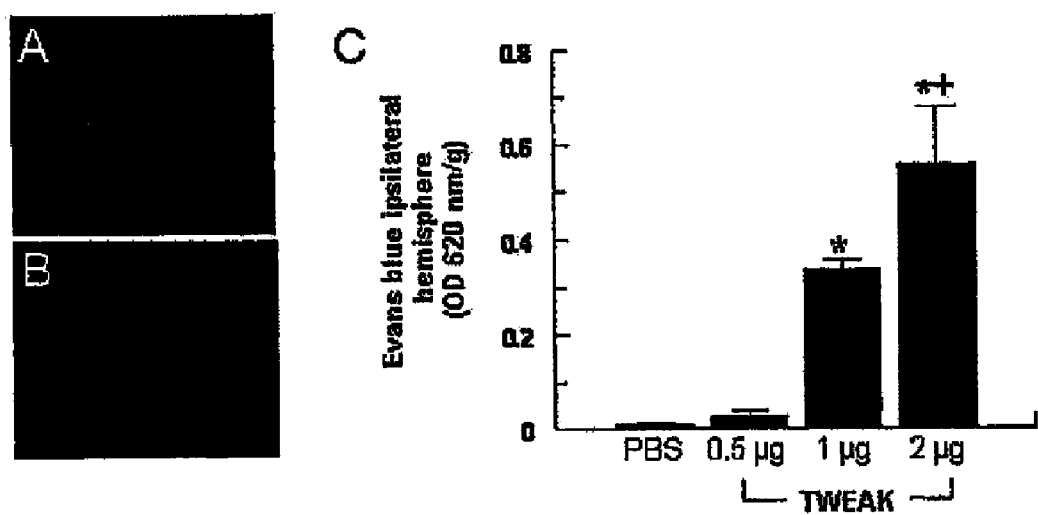

FIG. 16 shows that TWEAK induces a dose-dependent increase in BBB permeability.

Panels A & B: Evans blue dye extravasation following the intracerebral injection of 2 µg of TWEAK (A) or PBS (B). Blue is DAPI and red is Evans blue dye. Magnification ×100. Panel C: Quantification of Evans blue dye extravasation in response to intracerebral injection of either PBS or TWEAK. Bars denote means value (n=6–10) and error bars describe standard deviation of the mean. *p<0.00011 compared to PBS and 0.5 µg, +p 0.0005 compared to 1 µg.

Figure 17:
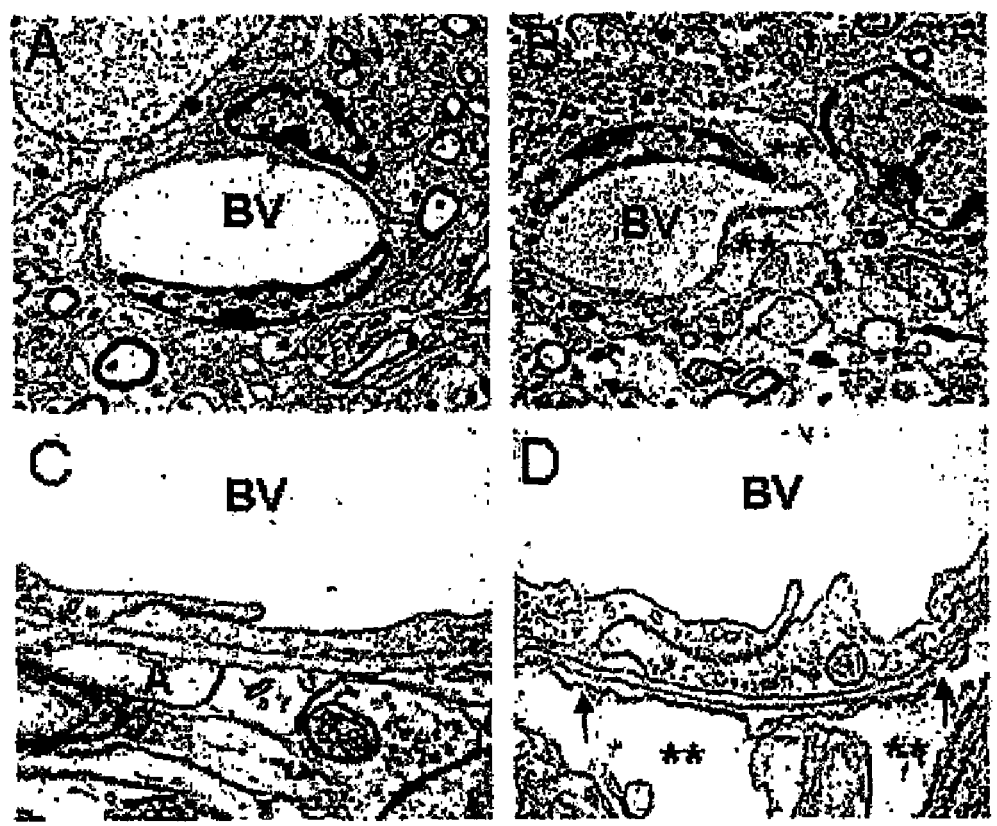

FIG. 17 shows that TWEAK disrupts the structure of the NVU.

Electron microscopy of cerebral arterioles in mouse brains injected with either PBS (panels A & C) or TWEAK (panels B & 1). The asterisks show fluid-fill spaces indicative of developing edema in the TWEAK-treated brain (panels B & D). The arrows indicate places in the neurovascular unit with disruption of the glia limitans and detachment of the astrocytic processes. BV: blood vessel; A: astrocytic processes. Magnification ×5000 in A & B and ×30000 in C & D.

Figure 18:
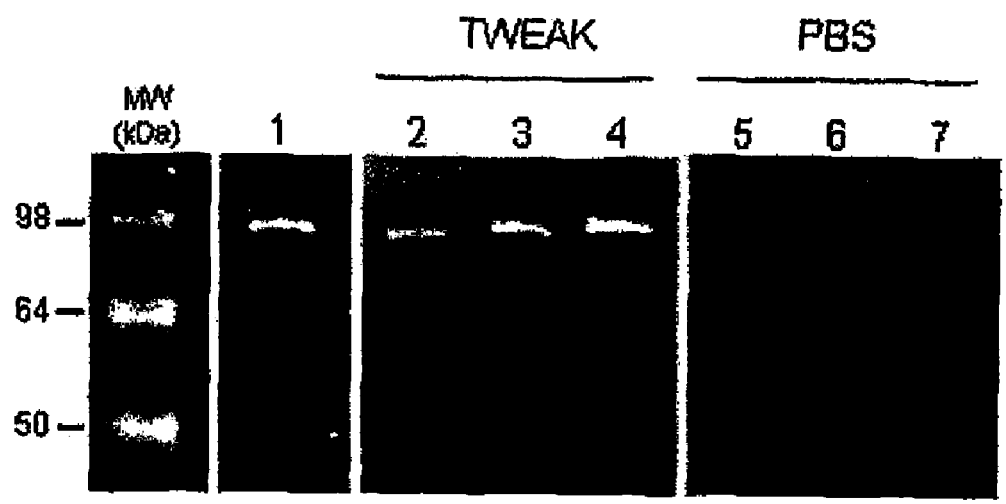

FIG. 18 shows that TWEAK increases MMP-9 activity in the brain.

Lane 1 is purified murine MMP-9 and all other lanes show MMF-9 activity after injection of either TWEAK (lanes 2, 3 & 4) or PBS (lanes 5, 6 & 7). Brains were extracted at 6 (lanes 2 & 5), 12 (lanes 3 & 6), or 24 hours (lanes 4 & &) after the intracerebral injections and gelatin zymography was performed.

Figure 19:
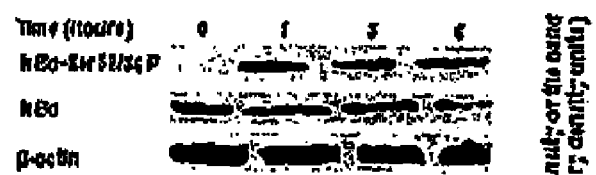
Figure 19:
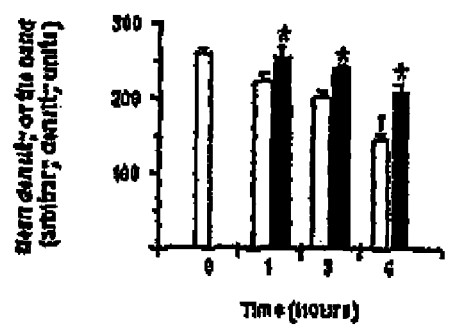
Figure 19:
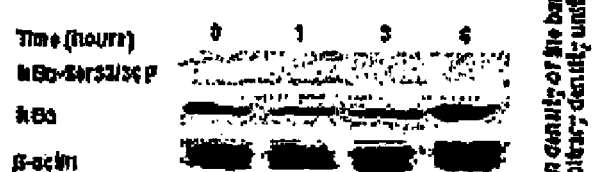
Figure 19:
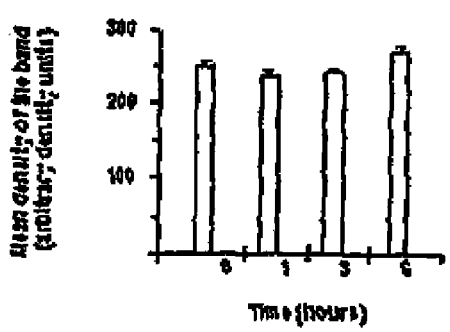

FIG. 19 shows the effect of TWEAK administration on NF-κB activation in the brain.

Panels A and B. Western blot analysis of IκBα phosphorylation and total IκBα expression in brain extracts 0, 1, 3 and 6 hours following the intracerebral injection of TWEAK (Panel A) or PBS (Panel B). Actin expression levels were also assayed as a control for protein loading.

Figure 20:
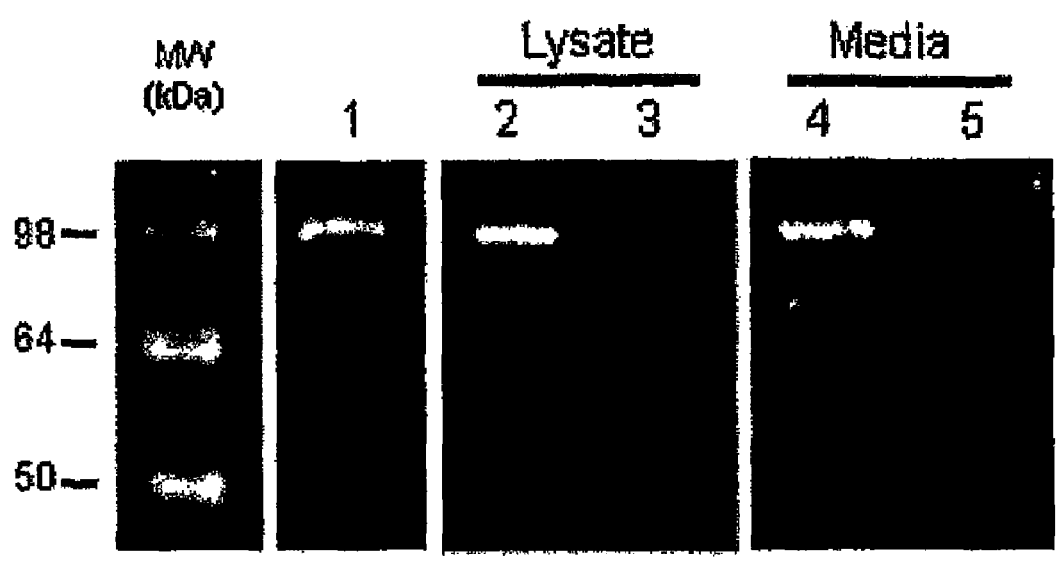

FIG. 20 shows that TWEAK treatment of murine astrocytes increases MMP-9 activity.

Gelatin zymography of cultured astrocytes treated with TWEAK or PBS. Lane 1 is purified murine MMP-9 and all other lanes show MMP-9 activity after exposure to either TWEAK (lanes 2 & 3) or PBS (lanes 3 & 5). Lanes 2 & 3 represent MMP-9 activity in cell lysates and lanes 4 & 5 depict MMP-9 activity in the corresponding media.

Figure 21:
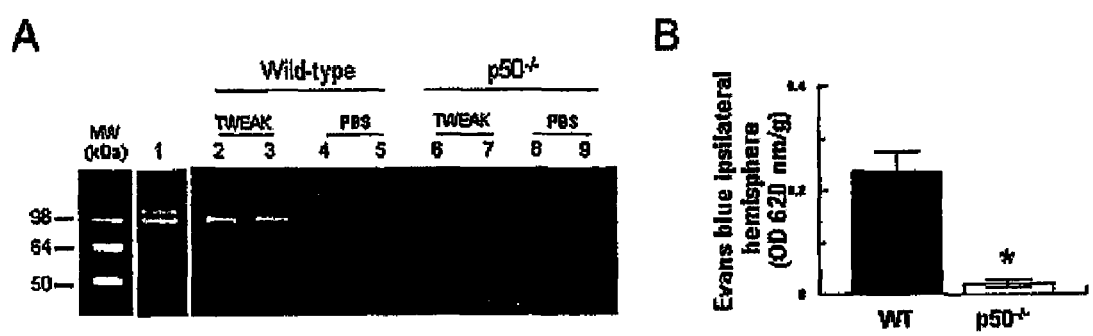

FIG. 21 shows that the NF-κB signaling pathway mediates TWEAK-induced MMP-9 activation and opening of the BBB.

Panel A: Gelatin zymography of brains treated with either TWEAK or PBS. Lane 1 is purified murine MMP-9. Lanes 2 through 5 show MMP-9 activity in wild-type mice injected with either TWEAK (lanes 2 & 3) or PBS (lanes 4 & 5). Lanes 6 through 9 show MMP-9 activity in $p50^{-/-}$ mice injected with either TWEAK (lanes 6 & 7) or PBS (lanes 8 & 9). Brains were harvested 24 hours after the injection of TWEAK or PBS. Panel B: Quantification of Evans blue dye extravasation 24 hours after the intracerebral injection of TWEAK in wild-type (WT) or p50 deficient $p50^{-/-}$) animals. Bars denote mean value (n–6) and error bars describe standard deviation of the mean. *p<0.005 compared to wild-type mice.

Figure 22:
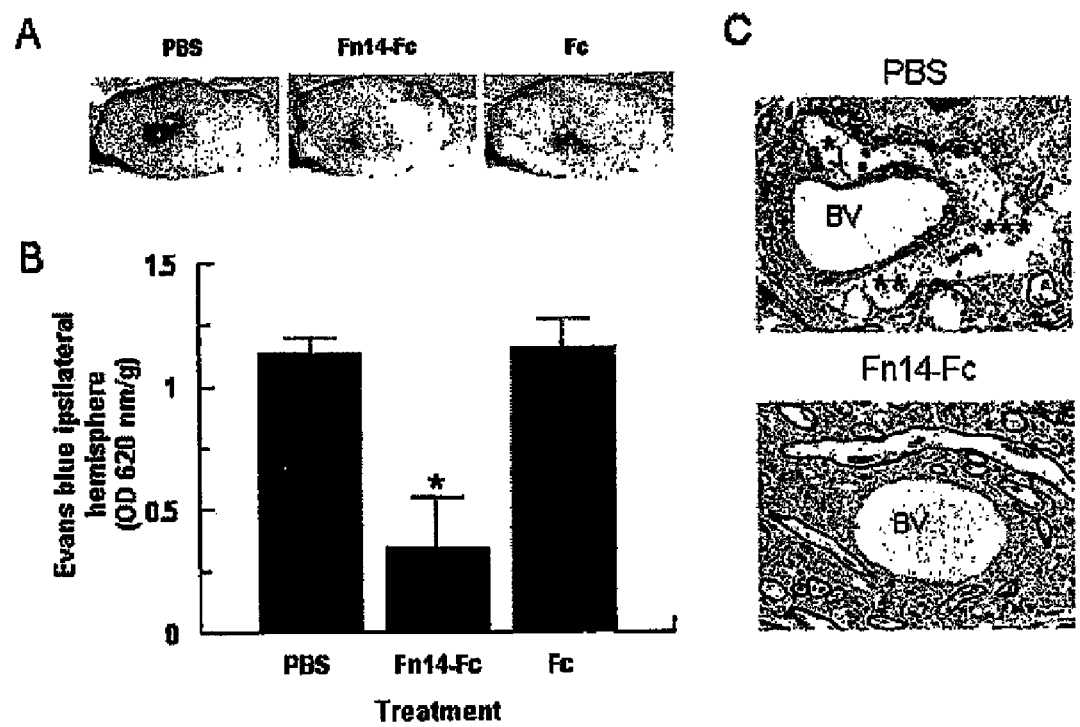

FIG. 22 shows the effect of endogenous TWEAK on the permeability of the BBB and the integrity of the NVU.

Panel A: Evans blue dye extravasation 72 hours after MCAO and the intraventricular injection of either PBS, Fn14-Fc or Fc. The blue staining denotes the areas with increased BBB permeability. Panel B: Quantification of Evans blue dye extravasation following MCAO and treatment with either PBS, Fn14-Fc or Fc. *p<0.05 compared to PBS- or Fc-treated brains (n–4). Panel C: Electron microscopy of cerebral capillaries of mouse brains subjected to MCAO and intraventricular administration of either PBS (top) or Fn14-Fc decoy (bottom). The asterisks show fluid-filled spaces indicative of developing edema in the PBS-treated brain. BV blood vessel. Magnification ×5000.

Figure 23:
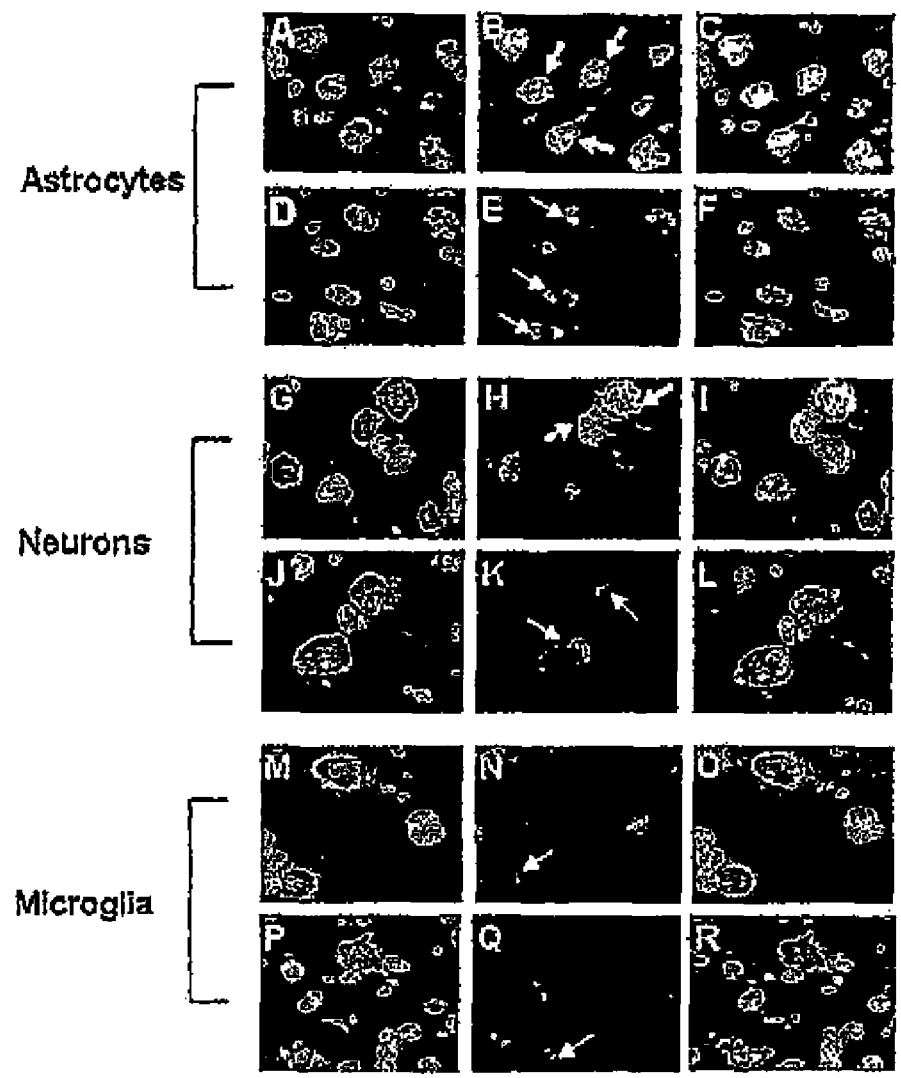

FIG. 23 shows effect of TWEAK on NF-κB pathway activation in astrocytes, neurons, and microglia.

Indirect immunofluorescence analysis of p65 subcellular location in murine astrocytes (A-F), neurons (G-L), and microglia (M-R), 1 h after the intracerebral injection of TWEAK, is shown. Frozen sections of brains injected with TWEAK (A-C, G-I, M-O) or PBS (D-F, J-L,P-R) are shown. Red is GFAP staining in A and D, neuronal (NeuN) staining in G and J, and MAC-1 staining in M and P. Blue is 4',6'-diamidino-2-phenylindole. Green is p65 staining in B, E, H, K, M, N, and Q, C, F, I, L, O, and R represent the corresponding merged images. Thick arrows indicate cells with nuclear translocation of the $p^{65}$ subunit. Thin arrows indicate the cytoplasmic location of the p65 subunit of the inactive NF-κB complex Magnification, 100×.

Figure 24:
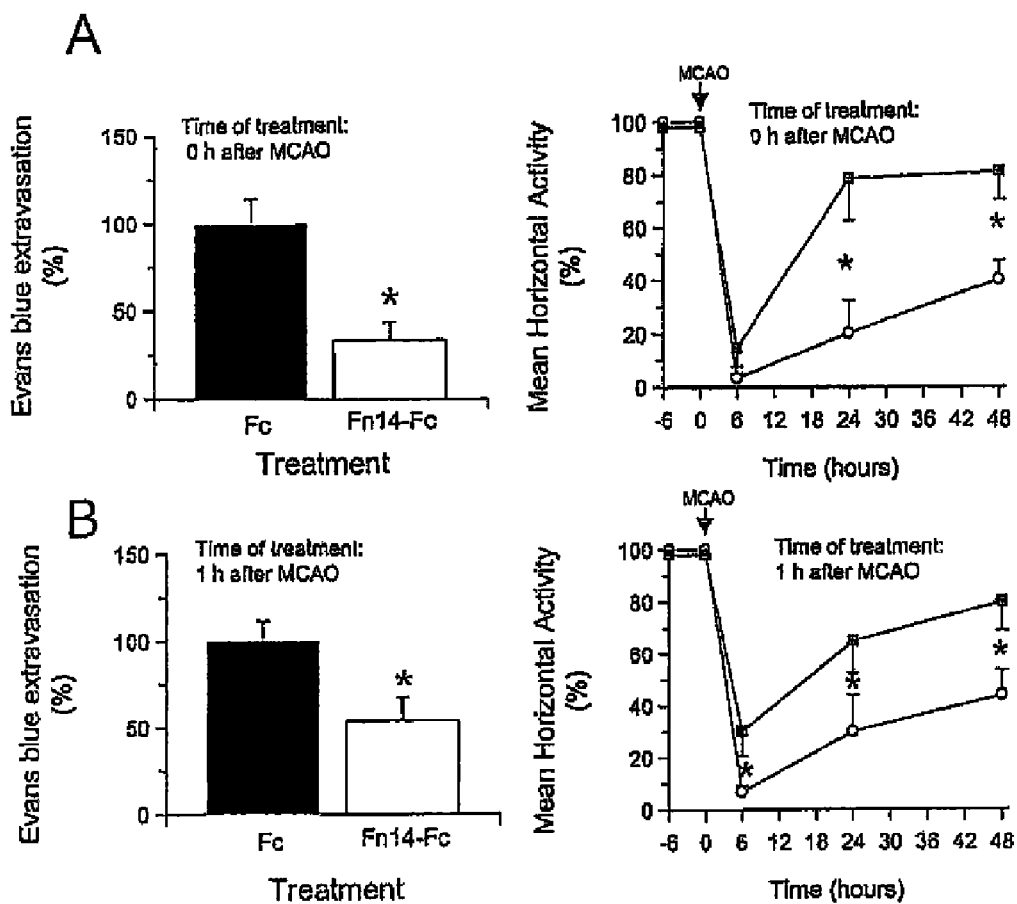

FIG. 24 shows that Fn14-Fc administration decreases cerebral edema and improves locomotor activity following MCAO.

A, left panel; Evans blue dye extravasation 48 hours after MCAO and treatment with either control Fc protein (black bar) or Fn14-Fc decoy protein (white bar) immediately after the onset of ischemia. A, right panel: Mean locomotor activity 6, 24 and 48 hours after MCAO and treatment with Fc (open circles) or Fn14-Fc (black boxes). N=4; *p<0.05. B: Repeat of experiment except Fc and Fn14-Fc were administered 1 hr after onset of ischemia. N=4; *p<0.05.

DETAILED DESCRIPTION OF THE INVENTION

Applicants disclose herein a therapeutic strategy aimed at attenuating the disruption of the BBB, and therefore, ameliorating the severity of vasogenic edema and significantly reducing the morbidity and mortality of patients with neurological diseases associated with increased permeability of the NVU. The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

As disclosed herein, NF-κB signaling and NF-κB-inducible gene products have been directly implicated in increased BBB permeability and cell death during cerebral ischemia (Bolton, S. J. et al., *Neuroscience* 86:1245-1257 (1998); Matsumoto, T. et al., *Lab. Invest.* 77:119-125; 45-48 (1997); Asahi, M et al., *J. Cereb. Blood Flow Metab.* 20:1681-1689 (2000); Asahi, M, *J. Neurosci.* 21:7724-7732(2001); Schneider, A., et al., *Nat. Med.* 5:554-559 (1999); Xu, L. et al., *Biochem. Biophys. Res. Commun.* 299:14-17 (2002)).

TWEAK and Fn14 expression have been associated with ischemia in both in vitro and in vivo models. For example, Potrovita et al. (Potrovita, I., *J. Neurosci.* 24:8237-8244 (2004)) reported that TWEAK and Fn14 mRNA levels increased when murine cortical neurons were subjected to oxygen glucose deprivation (an in vitro model of ischemia). The same researchers also found that TWEAK treatment of cortical neurons promoted NF-κB pathway activation and a ~2-fold increase in the number of cells with apoptotic features. Gene profiling (microarray) experiments revealed that Fn14 expression is up-regulated in two distinct in vivo models of axonal regeneration, sciatic nerve transection (Tanabe, K., *J. Neurosci.* 23:9675-9686 (2003)) and optic nerve injury (Fischer, D., *J. Neurosci.* 24:8726-8740 (2004)). In addition, Fn14 mRNA expression is induced in the ischemic hemisphere following MCAO in the mouse (Potrovita, I., *J. Neurosci.* 24:8237-8244 (2004); Trendelenburg, G., *J. Neurosci.* 22:5879-5888 (2002)). It was also found that the TWEAK mRNA levels increased slightly in response to cerebral ischemia and that intraperitoneal administration of a neutralizing anti-TWEAK monoclonal antibody reduced cerebral in (Potrovita, I., Supra (2004)).

Applicants have demonstrated that intracerebroventricular injection of a soluble Fn14-Fc decoy receptor immediately after MCAO significantly reduces the volume of the ischemic lesion and the extent of microglial cell activation and apoptotic cell death in the ischemic penumbra. Moreover, TWEAK alters BBB permeability by activating the NF-κB signaling pathway, which results in upregulation of MMP-9 (FIG. 21). These results indicate that the TWEAK-Fn14 signaling system contributes to cerebral ischemia-mediated brain damage in the mouse.

One aspect of the present invention relates to a method for treating neurological diseases associated with increase in the permeability of the BBB using an agent that interferes with TWEAK-Fn14 slanting. In one embodiment, the method comprises administering to a subject in need thereof an effective amount of an agent that inhibits Fn14 activity or Fn14 expression. In a preferred embodiment, the agent comprises an Fn14-Fc decoy receptor. In another embodiment, the agent comprises a neutralizing antibody to TWEAK or Fn14. In another embodiment, the agent comprises an antisense polynucleotide or an RNAi that inhibits TWEAK or Fn14 expression. In another embodiment the method comprises administering to a subject in need thereof an effective amount of an agent that inhibits Fn14 signal transduction. In yet another embodiment, the method further comprises co-administering to the subject an inhibitor of NF-κB-regulated biomolecule. In yet another embodiment, the method fiber comprises co-administering to the subject an effective amount of tPA. As used herein, a biomolecule is a naturally-occurring or synthetic molecule having bioactivity in a subject, such as a protein, a peptide, a saccharide, a polysaccharide, a nucleotide, a polynucleotide and a lipid. As used herein, the term "inhibit" refers to a substantial reduction of bioactivity or level of expression. For example, an agent inhibits the activity or expression of a biomolecule if the activity or expression of the biomolecule is reduced by 10%, 20%, 30%, 40%, 50%, 60%, 70% 80%, 90% or 100% in the presence of the agent.

Decoy Receptors

As is known in the art, a "decoy receptor" is a mutated or modified receptor that is capable of binding to an agonist or antagonist as the wild-type receptor, but lacks the ability to perform certain biological functions. Decoy receptors have been successfully used to inhibit the activity of various proteins. For example, a TNF receptor-Fc decoy that functions as a TNF-α antagonist is used for treatment of patients with rheumatoid arthritis (Olsen, N. et al., *N. Eng. J. Med.* 350: 2167-2179 (2004)). In one embodiment the decoy Fn14 receptor of the present invention comprises the extracellular, ligand-binding domain of Fn14. In a specific embodiment, the Fn-14 decoy receptor of the present invention comprises a fusion protein comprising the extracellular, lid-binding domain of Fn14 fused to the Fc portion and hinge region of the IgG1 heavy chain.

Antisense Polynucleotide

As is known in the art an "antisense polynucleotide" comprises a nucleotide sequence, which is complementary to a "sense polynucleotide" encoding a protein, e.g., complementary to the coding strand of a double-stranded cDNA molecule or complementary to an mRNA sequence. Accordingly, an antisense polynucleotide can hydrogen bond to a sense polynucleotide. The antisense polynucleotide can be complementary to an entire coding strand of a gene of the invention or to only a portion thereof. In one embodiment, an antisense polynucleotide molecule is antisense to a "coding region" of the coding strand of a nucleotide sequence of the invention. The term "coding region" includes the region of the nucleotide sequence comprising codons, which are translated into amino acid. In another embodiment the antisense polynucleotide molecule is antisense to a "noncoding region" of the coding strand of a nucleotide sequence of the invention.

Antisense polynucleotides of the present invention can be designed according to the rules of Watson and Crick base pairing. The antisense polynucleotide molecule can be complementary to the entire coding region of an mRNA corresponding to a gene of the invention, but more preferably is an oligonucleotide, which is antisense to only a portion of the coding or noncoding region. An antisense oligonucleotide can be, for example, about 5, 10, 15, 20, 25, 30, 35, 40, 45 or 50 nucleotides in length. An antisense polynucleotide of the invention can be constructed using chemical synthesis and enzymatic ligation reactions using procedures known in the art. For example, an antisense polynucleotide (e.g., an antisense oligonucleotide) can be chemically synthesized using naturally occurring nucleotides or variously modified nucleotides designed to increase the biological stability of the molecules or to increase the physical stability of the duplex formed between the antisense and sense polynucleotides, e.g., phosphorothioate derivatives and acridine substituted nucleotides can be used. Examples of modified nucleotides which can be used to generate the antisense polynucleotide include 5-fluorouracil, 5-bromouracil, 5-chlorouracil, 5-iodouracil, hypoxanthine, xantine, 4-acetylcytosine, 5-(carboxyhydroxyhnehyl) uracil, 5-carboxymethylaminomethyl-2-thiouridine, 5-carboxymethylaminomethyluracil dihydrouracil beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl2-thiouracil, beta-D-mannosylqueosine, 5'-methoxycarboxymethyluacil, 5-methoxyuracil, 2-methylthio-N6-isopentenyladen4exine, unacil-5-oxyacetic acid (v), wybutoxosine, pseudouracil, queosine, 2-thiocytosine, 5-methyl-2-thio-aracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil (acp3)w, and 2,6-diaminopurine. Alternatively, the antisense polynucleotide can be produced biologically using an expression Vector into which a polynucleotide has been subcloned in an antisense orientation (i.e., RNA transcribed from the inserted polynucleotide will be of an antisense orientation to a target polynucleotide of interest, described further in the following subsection).

The antisense polynucleotide molecules of the present invention are typically administered to a subject or generated in situ such that they hybridize with or bind to cellular mRNA and/or genomic DNA encoding the TWEAK and/or Fn14 protein to thereby inhibit expression of the protein, e.g., by inhibiting transcription and/or translation. The hybridization can be by conventional nucleotide complementarity to form a stable duplex, or, for example, in the cases of an antisense polynucleotide molecule which binds to DNA duplexes, through specific interactions in the major groove of the double helix. An example of a route of administration of antisense polynucleotide molecules of the invention is direct injection at a tissue site (e.g., intestine or blood). Alternatively, antisense polynucleotide molecules can be modified to target selected cells and then administrated systemically. The antisense polynucleotide molecules can also be delivered to cells using the vectors described herein. To achieve sufficient intracellular concentrations of the antisense molecules, vector constructs in which the antisense polynucleotide molecule is placed under the control of a strong promoter are preferred.

RNAi

RNA inference ("$RNA_i$") is a phenomenon of the introduction of double-stranded RNA (dsRNA) into certain organisms and cell types causing degradation of the homologous mRNA. RNAi was first discovered in the nematode *Caenorhabditis elegans*, and it has since been found to operate in a wide range of organisms. In recent years, RNAi has becomes an endogenous, efficient and potent gene-specific silencing technique that uses double-stranded RNAs (dsRNA) to mark a particular transcript for degradation in vivo. $RNA_i$ technology is disclosed, for example, in U.S. Pat. No. 5,919,619 and PCT Publication Nos. WO99/14346 and WO01/29058.

Briefly, dsRNAs 21-25 nucleotides long, called short interfering RNAs (siRNA), are introduced into the cell. SiRNAs may also be produced endogenously by degradation of long sRNA molecules by an RNAse III-related nuclease called Dicer. Once formed, the siRNAs assemble with protein components into an RNA-induced silencing complex (RISC). An ATP-generated unwinding of the siRNA activates the RISC, which in turn targets the homologous mRNA transcript by Watson-Crick base-pairing and cleaves the mRNA. This sequence specific degradation of mRNA results in gene silencing.

Antibodies

Antibodies suitable to the present invention include isolated polyclonal and monoclonal antibodies. Preferably for therapeutic use in a subject, the antibodies are humanized, as per the description of antibodies described below.

A target antigen (e.g., TWEAK or Fn14), or a portion or fragment thereof, can be used as an immunogen to generate antibodies that bind the antigen using standard techniques for polyclonal and monoclonal antibody preparation. The immunogen should be an antigenic peptide comprising at least 8 amino acid residues, and encompasses an epitope of the target antigen such that an antibody raised against the peptide forms a specific immune complex with the target antigen. Preferably, the antigenic peptide comprises at least 8 amino acid residues, more preferably at least 12 amino acid residues, even more preferably at least 16 amino acid residues, and most preferably at least 20 amino acid residues.

Immunogenic portions (epitopes) may generally be identified using well-known techniques. Such techniques include screening polypeptides for the ability to react with antigen-specific antibodies, antisera and/or T-cell lines or clones. As used herein, antisera and antibodies are "antigen-specific" if they bind to an antigen with an affinity of $10^5$ $M^{-1}$ or greater. Such antisera and antibodies may be prepared as described herein, and using well-known techniques. An epitope of an antigen is a portion that reacts with such antisera and/or T-cells at a level that is not substantially less than the reactivity of the full-length polypeptide (e.g., in an ELISA and/or T-cell reactivity assay). Such epitopes may react within such assays at a level that is similar to or greater than the reactivity of the full-length polypeptide. Such screens may generally be performed using methods well known to those of ordinary skill in the art. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Preferred epitopes encompassed by the antigenic peptide are regions of a target antigen that are located on the surface of the protein, e.g., hydrophilic regions, as well as regions with high antigenicity.

An immunogen typically is used to prepare antibodies by immunizing a suitable subject, (e.g., rabbit, goat, mouse or other mammal) with the immunogen. An appropriate immunogenic preparation can contain, for example, recombinantly expressed antigen or a chemically synthesized antigen. The preparation can further include an adjuvant, such as Freund's complete or incomplete adjuvant, or similar immunostimulatory agent immunization of a suitable subject with an immunogenic peptide preparation induces a polyclonal antibody response. Techniques for preparing, isolating and using antibodies are well known in the art.

The antibodies of the present invention include F(ab) and F(ab')$_2$ fragments which can be generated by treating the antibodies with an enzyme such as pepsin. The antibodies also include "single-chain Fv" or "scFv" antibody fragments. The scFv fragments comprise the $V_H$ and $V_L$ domains of antibody, wherein these domains are present in a single polypeptide chain Generally, the Fv polypeptide further comprises a polypeptide linker between the $V_H$ and $V_L$ domains, which enables the scFv to form the desired structure for antigen binding.

In certain specific embodiments, the antibody of the present invention is an Fc portion and/or hinge region of an IgG1 heavy chain.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

Humanized antibodies are particularly desirable for therapeutic treatment of human subjects. Humanized forms of non-human (e.g. murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues forming a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general the humanized antibody will comprise substantially au of at least one, and typically two, variable domains, in which all or substantially all of the CDR regions correspond to those of a non-human immunoglobulin and an or substantially all of the constant regions being those of a human immunoglobulin consensus sequence. The humanized antibody will preferably also comprise at least a portion of an immunoglobulin constant region (Fc), typically that of a human immunoglobulin. In certain embodiments, the Fc portion the IgG1 heavy chain is employed in the present invention.

Such humanized antibodies can be produced using transgenic mice which are incapable of expressing endogenous immunoglobulin heavy and light: chain genes, but which can express human heavy and light chain genes. The transgenic mice are immunized in the normal fashion with a selected antigen, e.g., all or a portion of a polypeptide corresponding to TWEAK or Fn14. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies.

Humanized antibodies, which recognize a selected epitope, can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to a target antigen are capable of reducing or eliminating the biological function of the target antigen, as is described below. That is, the addition of the anti-target antigen antibodies (either polyclonal or preferably monoclonal) to the target antigen may reduce or eliminate the bioactivity of the target antigen. Generally, at least a 25% decrease in activity is preferred, with at least about 50% being particularly preferred and about a 95-100% decrease being especially preferred.

Expression Vectors

The expression vectors of the present invention pertains to vectors capable of in vitro and/or in vivo expression of a polynucleotide or a polypeptide that directly or indirectly inhibits the activity of TWEAK, Fn14 or other components of the TWEAK/Fn14 signaling pathway. One type of vector is a "plasmid," which includes a circular double stranded DNA loop into which additional DNA segments can be ligated. In the present specification, "plasmid" and "expression vector" can be used interchangeably as the plasmid is the most commonly used form of vector. However, the invention is intended to include such other forms of expression vectors, such as viral vectors.

The expression vectors of the present invention comprise one or more regulatory sequences, which is operatively linked to the polynucleotide sequence to be expressed. The expression vectors of the invention can be introduced into a target tissue to thereby produce proteins or peptides, including fusion proteins or peptides, in the target tissue.

The term "regulatory sequence" refers collectively to promoter sequences, polyadenylation signals, transcription termination sequences, upstream regulatory domains, origins of replication, internal ribosome entry sites ("IRES"), enhancers, and the like, which collectively provide for the replication, ascription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that are sufficient for RNA polymerase recognition, binding and transcription initiation. Additionally, a promoter includes sequences that modulate the recognition, binding and transcription initiation activity of RNA polymerase. Such sequences may be cis acting or may be responsive to transacting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney marine leukemia virus (MMLV) promoter, phosphoglycerate kinase (PGK) promoter, muscle creatine kinase (MCK) promoter, myosin promoter, α-actin promoter and the like.

The term "operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

In another embodiment the expression vector is capable of directing expression of the polynucleotide preferentially in a particular cell type (e.g., tissue-specific regulatory elements are used to express the polynucleotide). Tissue-specific regulatory elements are known in the art and may include epithelial cell-specific promoters. Other non-limiting examples of suitable tissue-specific promoters include neuron-specific promoters (e.g., the neurofilament promoter).

The invention provides a recombinant expression vector comprising a polynucleotide encoding a target protein cloned into the expression vector in an antisense orientation. That is, the DNA molecule is operatively linked to a regulatory sequence in a manner, which allows for expression (by transcription of the DNA molecule) of an RNA molecule which is antisense to mRNA corresponding to the target protein. Regulatory sequences operatively linked to a polynucleotide cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense polynucleotides are produced under the control of a high efficiency regulatory region, the activity of which can be determined by the cell type into which the vector is introduced.

The invention further provides viral vectors and, more preferably, a retrovirus, lentivirus, adenovirus, adeno-associated virus (AAV), herpes virus, or alphavirus vectors. The viral vector can also be an astrovirus, coronavirus, orthomyxovirus, papovavirus, paramyxovirus, parvovirus, picornavirus, poxvirus, togavirus vector.

In addition to virus-mediated gene delivery, other delivery methods and media may be employed such as, for example, nucleic acid expression vectors, polycationic condensed DNA linked or unlinked to killed adenovirus alone, for example see Curiel, *Hum Gene Ther* 3:147-154 (1992) ligand linked DNA, for example, see Wu, *J. Biol. Chem* 264:16985-16987 (1989), eukaryotic cell delivery vehicles cells, for example see U.S. Ser. No. 08/240,030, filed May 9, 1994, and U.S. Ser. No. 08/404,796, deposition of photopolymerized hydrogel materials, handheld gene transfer particle gun, as described in U.S. Pat. No. 5,149,655, ionizing radiation as described in U.S. Pat. No. 5,206,152 and in PCT Patent Publication No. WO 92/11033, nucleic charge neutralization or fusion with cell membranes. Additional approaches are described in Philip, *Mol. Cell. Biol.* 14:2411-2418 (1994) and in Woffendin, *Proc. Natl. Acad Sci.* 191:581-585 (1994). Particle mediated gene transfer may be employed, for example see U.S. provisional application Ser. No. 60/023, 867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu, *J. Biol. Chem* 262:4429-4432 (1987), insulin as described in Hucked, *Biochem. Pharmacol.* 40:253-263 (1990), galactose as described in Plank Bioconjugate *Chem* 3:533-539 (1992), lactose or transferrin Naked plasmid DNA may also be employed. Exemplary naked DNA introduction methods are described in PCT Patent Publication No, WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA no the cytoplasm. Liposomes that can act as gene delivery vehicles are described in U.S. Pat. No. 5,422,120, PCT Patent Publication Nos. WO 95/13796, WO 94/23697, and WO 91/144445, and EP No. 524,968.

The invention also provides chimeric or fusion proteins. In a preferred embodiment a fusion protein comprises at least one biologically active portion of a component of the TWEAK/Fn14 signaling pathway (hereinafter the "TWEAK/Fn14-related polypeptide"). Within the fusion protein, the term "operatively linked" is intended to indicate that the TWEAK/Fn14-related polypeptide and the non-TWEAK/Fn14-related polypeptide are fused in-frame to each other. The non-TWEAK/Fn14-related polypeptide can be fused to the N-terminus or C-terminus of the TWEAK/Fn14-related polypeptide.

A peptide linker sequence may be employed to separate the TWEAK/Fn14-related polypeptide from non-TWEAK/Fn14-related polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the TWEAK/Fn14-related polypeptide and non-TWEAK/Fn14-related polypeptide, and (3) the lack of hydrophobic or charged residues that might react with the polypeptide frictional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the TWEAK/Fn14-related polypeptide and non-TWBAW/Fn14-related polypeptide have non-essential N-terminal amino acid regions that can be used to separate the functional domains and prevent steric interference.

For example, in one embodiment, the fusion protein is the extracellular, ligand-binding domain of Fn14 fused to the Fc portion and hinge region of the IgG1 heavy chain (termed "Fn14/IgG1 Fc fusion protein". In another embodiment the Fn14/IgG1 Fc fusion protein her contains a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment a polynucleotide sequence encoding a signal sequence can be operably linked in an expression vector to a protein of interest, such as a protein, which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art-recognized methods. Alternatively, the signal sequence can be linked to the protein of interest using a sequence, which facilitates purification, such as with a GST domain.

The TWEAK/Fn14 fusion proteins of the present invention can be incorporated into pharmaceutical compositions and administered to a subject in vivo, as described herein. The fusion proteins can be used to affect the bioavailability or to facilitate the purification of the TWEAK/Fn14-related polypeptide.

The TWEAK/Fn14 fusion proteins of the present invention can be used as immunogens to produce antibodies. The TWEAK/Fn14-fusion proteins used as immunogens may comprise a non-TWEAK/Fn14 immunogenic protein. Preferably the immunogenic protein is capable of eliciting a recall response.

Preferably, a TWEAK/Fn14-chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini filling of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, many expression vectors are commercially available, that already encode a fusion moiety (e.g., a GST polypeptide). A TWEAK/Fn14 polypeptide-encoding polynucleotide can be cloned into such an expression vector such that the fusion moiety is linked in-frame to the TWEAK/Fn14 polypeptide-encoding polynucleotide.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the ammo terminus of the recombinant protein. Such fusion vectors typically serve three purposes: 1) to increase expression of recombinant protein; 2) to increase the solubility of the recombinant protein; and 3) to aid in the purification of the recombinant protein by awing as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein.

One strategy to maximize recombinant protein expression in *E. coli* is to express the protein in a host bacteria with an impaired capacity to proteolytically cleave the recombinant protein. Another strategy is to alter the polynucleotide sequence of the polynucleotide to be insert into an expression vector so that the individual codons for each amino acid are those preferentially utilized in *E. coli*. Such alteration of polynucleotide sequences of the invention can be carried out by standard DNA synthesis techniques.

The expression vector of the present invention can be a yeast expression vector or a baculovirus expression vector. Examples of vectors for expression in yeast *S. cerevisiae* include pYepSec1, pMFa, pJRY88, pYES2 (In Vitrogen Corporation, San Diego, Calif.), and picZ (In Vitrogen Corp, San Diego, Calif.). Baculovirus vectors available for expression of proteins in cultured insect cells (e.g., Sf9 cells) include the pAc series and the pVL series.

For purposes of this invention, an effective amount of an agent that inhibits Fn14 activity or Fn14 expression is an amount that is sufficient to palliate, ameliorate, stabilize, reverse, slow or delay the progression of the ischemic-inducted BBB breakdown or brain injury. Some individuals are refractory to these treatments, and it is understood that the methods encompass administration to these individuals. The amount to be given will be determined by the condition of the individual, the extent of disease, the route of administration, how many doses will be administered, and the desired objective.

Assessment of the efficacy of a particular treatment regimen may be determined by any of the techniques known in the art, including diagnostic methods such as imaging techniques, biopsy, and/or an evaluation of the presence, absence or amelioration of ischemia-associated symptoms. It will be understood that a given treatment regime may be modified, as appropriate, to maximize efficacy.

Pharmaceutical Compositions

Another aspect of the present invention relates to a composition for preventing the development of cerebral edema in several neurological diseases including acute cerebral ischemia. In one embodiment; the composition comprises an agent that inhibits Fn14 activity or Fn14 expression and a pharmacologically acceptable carrier. In a preferred embodiment, the agent comprises an Fn14-Fc decoy receptor. In another embodiment, the agent comprises an inhibitor of TWEAK or Fn14 expression. In another embodiment, the agent is an antibody to TWEAK or Fn14 that prevents TWEAK-Fn14 interactions. In another embodiment, the composition further comprises an inhibitor of NF-κB-regulated proteins such as IL-1, IL-6, IL-8 and MMP-9. In yet another embodiment, the composition further comprises tPA.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include intravenous, intradermal subcutaneous, oral, and transmucosal administration. Solutions or suspensions used for intravenous, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

In all cases, the injectable composition should be sterile and should be fluid to the extent that easy syringability exists. It should be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol sodium chloride in the composition. Prolonged absorption of the injectable compositions can be brought about by including in the composition an agent which delays absorption, for example, aluminum monostearte and gelatin.

Sterile injectable solutions can be prepared by incorporating the active compound or agent (e.g., an inhibitor of Fn14) in the required amount in an appropriate solvent with one or a combination of ingredients enumerated above, as rued, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the battier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

In one embodiment the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the at of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system & at targets such compounds to the site of affected tissue in order to minims potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured for example, by high performance liquid chromatography.

Pharmaceutical compositions appropriate for clinical applications must be stable under the conditions of manufacture and storage and must be preserved against the contaminating action of microorganisms such as bacteria and fungi.

The present invention is further illustrated by the following examples which should not be construed as limiting. The contents of all references, patents and published patent applications cited throughout this application, as well as the Figures and Tables are incorporated herein by reference.

EXAMPLE 1

Animal Models of Cerebral Ischemia (1) Model 1: Middle Cerebral Artery Occlusion (MCAO) without Reperfusion in Mice In this model (Nagai N. et al, *Circulation,* 99:2440-2444 (1999); Yepes, M et al., *J. Clin. Invest.* 112:1533-1540 (2003)) as are anesthetized and an incision is made between the left ear and the left eye. A 2 mm burr hole is opened 2 cm anterior to the foramen ovale. A small incision is made over the dura and the middle cerebral artery is then exposed and occluded with a 10-0 suture at its crossing point with the inferior cerebral vein. This model yields a very well defined and reproducible area of ischemia and it is the method of choice when the effects of reperfusion should be eliminated (i.e., to study the effects of endogenous, intracerebral TWEAK).

(2) Model 2: Embolic Occlusion of the Middle Cerebral Artery in Mice

In this model (Zhang, Z et al., *J. Cereb. Blood Flow Metab.* 17:1081-1088 (1997)), femoral artery blood from a donor mouse is withdrawn and retained in 10 cm of a PE-50 tube for 2 hours at room temperature and for 22 hours at 4 degrees C. Five cm of the PE-50 tubing containing the clot are then cut and attached to a system built of two syringes interconnected by 40 cm of PE-10 tube filled with saline. The clot is continuously shifted from one syringe to the other for 5 minutes. A single clot is then transferred to a modified PE50 catheter filled with saline solution. The animal is placed under anesthesia and under the operating microscope a midline incision is made in the upper portion of the chest. The right common carotid artery (CCA), the right external carotid arty (ECA) and the right internal carotid artery (ICA) are isolated and carefully separated from the adjacent vagus nerve. A 6-0 suture is loosely tied at the origin of the ECA and a second suture is ligated at the distal end of the ECA. The CCA and the ICA are then temporarily clamped using a curved microvascular clip. A modified PE-50 catheter (0.15-0.18 mm diameter) containing a clot is attached to a 10 µl Hamilton syringe and introduced into the ECA lumen through a small puncture. The suture around the origin of the ECA is tightened around the intraluminal catheter to prevent bleeding, and the microvascular clip is removed. An 8-mm length catheter is then advanced from the ECA into the lumen of the ICA. At this point, the intraluminal catheter is at 1-1.5 mm from the origin of the middle cerebral artery. The embolus is then gently injected through the catheter followed by immediate extraction of the modified PE-50 catheter. This method yields a cortical and subcortical area of ischemia. This model of focal ischemia and reperfusion permits study of the effect of thrombolytics in acute cerebral ischemia, and is very similar to the situation observed in humans with acute embolic stroke.

Animals are then allowed to recover and after different time points brains are fixed by transcardiac perfusion with paraformaldehyde (4%), and then, surgically removed and rapidly frozen. To measure the volume of cerebral ischemia, sections are cut and stained with hemamtoxlin and eosin or with TTC (2,3,5-tiphenyltetrazolium chloride). Sequential 5 um sections are then analyzed and the ischemic area is calculated using an Image Analyzer System (Scion Inc.). The optical densities of unlesioned cortex and basal ganglia are defined and then used as the threshold value for the recognition of normal gray matter by the image analyzer system, as all non-infarcted gray matter areas have optic densities equal to or greater than these threshold values. From these data, the areas of ischemia are then summed over the number of sections evaluated and the respective volumes are calculated by multiplying each sum by the distance between sections. The volume of the ischemic lesion is measured by magnetic resonance imaging (diffusion weighted images [DWI] and T2 images).

EXAMPLE 2

TWEAK and Fn14 Expression in the Normal Central Nervous System

The expression of TWEAK and Fn14 in normal mouse brain tissue was observed using immunohistochemical analysis. In the mouse brain TWEAK immunoreactivity was detected mainly in endothelial cells of medium and small caliber blood vessels, and in cells with morphological features of astrocytes that were located mainly in the periphery of the blood vessels. Fn14 immunoreactivity was detected primarily in neurons in the frontal, parietal and occipital cortex, and in Purkinje cells in the cerebellum (FIG. 4). To determine if this pattern of TWEAK and Fn14 expression is also observed in the human CNS, an RNA dot blot containing normalized loading levels of poly (A)+RNA isolated from different anatomical regions of the normal brain was obtained from Clontech Inc. and hybridized to an Fn14 cDNA probe. Our results showed Fn14 mRNA expression in different areas of the normal human CNS mainly in the occipital lobe, caudate nucleus, temporal lobe, putamen, substantia nigra, and spinal cord (FIG. 5).

Immunohistochemical analysis using commercial available normal human brain sections (Novagen) was also performed. Applicants observed TWEAK immunostaining in endothelial cells of medium and small caliber blood vessels, as well as in selective cellular groups with morphological features of glial cells throughout the cortex and in the brainstem. In contrast Fn14 immunoreactivity was detected mainly in cortical neurons, as well as in cells with features of perivascular microglia (FIG. 6). Together, these results demonstrate that TWEAK and Fn14 are expressed in the normal brain (mouse and human). However, whereas TWEAK immunostaining is observed predominantly in endothelial cells and astrocytes, Fn14 immunostaining is most prominent in non-vascular cells, in particular cells with morphological features of neurons and microglia.

EXAMPLE 3

Effect of Cerebral Ischemia on TWEAK and Fn14 Gene Expression

Following the onset of focal cerebral ischemia there is the formation of a densely ischemic region known as the ischemic core, where blood flow is reduced to <15%, surrounded by a penumbral region where blood flow is decreased to <40% (Nedergaard, M., J. Cereb. Blood Flow Metab. 6:414-424 (1986)). In the penumbral area, the cerebral blood flow is sufficiently decreased to abolish electrical potentials yet sufficient to allow maintenance of membrane potentials and cellular ionic homeostasis (Hakim, A. M. Can. J. Neurol. Sci. 14:557-559 (1987)). Several events have been described in the zone of ischemic penumbra, including excitotoxicity and apoptotic cell death (Garcia, J. H., et al., Acta Neuropathol. (Berl) 43:85-95 (1978); Barber, P. A. et al., Adv. Neurol. 92:151-164 (2003); Dirnagl, U., et al., Trends Neurosci. 22:391-397 (1999); and Lee, J. M., et al., Nature 399: A7-14 (1999)), and if the ischemic insult is persistent, this potentially salvageable area becomes infarcted. To determine whether TWEAK or Fn14 mRNA expression levels were regulated in response to cerebral ischemia, RNA was isolated from ipsilateral (ischemic) and contralateral (non-ischemic) hemispheres dissected from mice sacrificed at different time points following MCAO (0, 24, 48 or 72 hours). Real-time quantitative RT-PCR analysis revealed that TWEAK mRNA levels in both hemispheres remained relatively constant during the course of the experiment (FIG. 7A). However, a statistically significant increase was observed in Fn14 mRNA levels in the ipsilateral, ischemic hemisphere at all three time points, with peak induction at 48 hours (2.3-fold increase over baseline) (FIG. 7B).

TWEAK and Fn14 protein expression levels and distribution in the ipsilateral and contralateral hemispheres were compared by immunohistochemical staining of mice brains at 0, 24, 48 and 72 hours following permanent MCAO. TWEAK immunoreactivity was detected in the ipsilateral hemisphere in the region surrounding the necrotic core (i.e., the ischemic penumbra). This staining was most intense at 48 hours following MCAO and much lower in the corresponding region of the non-ischemic contralateral hemisphere FIG. 8). An increase in TWEAK protein expression but not TWEAK mRNA expression was observed under these experimental conditions. One possible explanation is that TWEAK mRNA expression increased and ten rapidly returned to baseline levels by 24 hours, which was the first time point that the mRNA level was examined. Fn14 immunoreactivity was also detected in the ipsilateral hemisphere and the staining was most intense in the ischemic penumbra at 48 hours following MCAO and significantly lower in the corresponding region of the contralateral hemisphere FIG. 9). Staining of die ischemic penumbra region was not detected when control rabbit IgG was used instead of anti-TWEAK or anti-Fn14 IgG as the primary immunological reagent Together, these results demonstrate that cerebral ischemia promotes an increase in TWEAK and Fn14 expression in the area of the ischemic penumbra.

In an exemplary embodiment, gene expression levels are determined in the different cellular elements of the neurovascular unit, under both non-ischemic and ischemic conditions in vivo. To determine which cell types express TWEAK and Fn14 following MCAO, confocal immunofluorescent microscopy is performed using sections from both non-ischemic and ischemic brains. Mice undergo MCAO and brains will be extracted and embedded in paraffin 0, 24, 48 and 12 hours later. Sections (5 μn cuts) are stained for TWEAK and Fn14 and co-stained with either rabbit anti-von Willebrand factor (VWF) antibodies (marker for endothelial cells: purchased from BioDesign), rabbit anti-glial fibrillary acidic protein (GFAP) antibodies (marker for astrocytes; Dako), mouse anti-Mac-1 monoclonal antibodies (marker for microglial cells), or mouse anti-neuronspecific nuclear protein (NeuN) monoclonal antibodies (marker for neurons; Chemicon). Goat anti-rabbit secondary antibodies conjugated to Alexa 488 (Molecular Probes) and donkey anti-mouse or anti-goat secondary antibodies conjugated to Rhodamine Red-X (Jackson ImmunoResearch) may be used as secondary antibodies. In some cases, the cells are counterstained with DAPI (Molecular Probes). The ipsilateral, ischemic hemisphere (necrotic core as well as in the area of ischemic penumbra) are compared to the contralateral, non-ischemic hemisphere and to brain cuts obtained from non-ischemic brains.

EXAMPLE 4

TWEAK and Fn14 Expression in Nonischemic Monoculture Systems

To further characterize the expression of TWEAK and Fn14 in CNS cells, primary neuronal and astrocyte cultures were prepared and stained for TWEAK and Fn14 expression. Microglial cells were also cultured using the protocol of McCarthy and de Vellis McCarthy, K. D. et al., *J. Cell Biol.* 85:890-902 (1980)) and identified by the presence of Mac-1 immunoreactivity using a monoclonal antibody kindly provided by Dr Li Zhang (University of Maryland School of Medicine). Neurons, astrocytes and microglial cells expressed both TWEAK and Fn14. However, the highest level of TWEAK immunostaining was detected in astrocytes and the highest level of Fn14 immunostaining was detected in neurons and microglia FIG. 10). These observations suggest "cross-talk" between astrocytes, neurons and microglial cells in the CNS where TWEAK released from astrocytes could bind to the Fn14 receptors on neurons and microglial cells.

EXAMPLE 5

Effect of TWEAK Treatment on Microglial Cells

It has been demonstrated that TWEAK binding to Fn14 activates the NF-κB pathway (Donohue, P. J. et al., *Arterio-scier. Thromb. Vasc. Biol.*, 23:594-600 (2003); Kim, S. H. et al., *Circ. J.*, 68:396-399 (2004); , S. et al., *Biochem. Biophys. Res. Commun.*, 305:789-796 (2003); and Nin, L. et al., *J. Invest. Dermatol.*, 122:1175-1179 (2004)) and induces the expression of various NE-κB-regulated genes (e.g., IL-6, IL-8, MMP-9, ICAM-1) (Chicheportiche, Y. et al., *J. Biol. Chem.*, 272:32401-32410 (1997); Lynch, C. N. et al., *J. Biol. Chem.*, 274:8455-8459 (1999); Harada, N. et al., *Biochem. Biophys. Res. Commun.*, 299:488-493 (2002); Nakayama, M. et al., *J. Immunol.*, 168:734-743 (2002); Nakayama, M. et al., *J. Immunol.*, 170:341-348 (2003); and Kawakita, T. et al., *Biochem. Biophys. Res. Commun.*, 318:726-733 (2004)). Recently it has been reported that TWEAK treatment of marine cortical neurons stimulates NF-κB activation (Potrovita, I. et al., *J. Neurosci.*, 24:8237-8244 (2004)) but the effect on microglial cells has not been reported. To examine whether TWEAK was able to activate the NF-κB pathway when added to murine cortex-derived microglial cells were cultured as described above and incubated with TWEAK (100 ng/ml) for 0, 30, 60 or 120 minutes.

Cells were permeabilized with saponin and immunofluorescence analysis was then performed using an anti-p65 antibody (Santa Cruz Biotechnology) and a donkey anti-rabbit rhodamine conjugate secondary antibody (Jackson Immunoresearch). TWEAK treatment induced translocation of p65 from the cytoplasmic compartment to the nuclear compartment, an indicator of NF-κB pathway activation. These results support applicants teaching that the TWEAK released from astrocytes following cerebral ischemia might interact with the Fn14 receptors on microglial cells with resultant activation of the NF-κB pathway.

EXAMPLE 6

Production and Characterization of a Soluble Fn14-Fc Decoy Receptor

An Fn14-Fc fusion protein was prepared, in which the extracellular, ligand-binding domain of Fn14 is fused to the Fc portion and hinge region of the IgG1 heavy chain (FIG. 11). Briefly, a plasmid pSecTag2/Fn14-Fc was constructed and a stably-transfected human embryonic kidney (HEK) 293T clonal cell line was isolated as described (Donohue P J, et al., 2003, *Arterioscler. Thromb. Vasc. Biol.*, 23: 594-600). To construct the plasmid pSecTag2/Fc, the plasmid pSecTag2/OPG-Fc (provided by M. Tondravi, NIH) was digested with SfiI to release the OPG cDNA insert. The DNA ends were fined in using T4 DNA Polymerase and then the plasmid was self-ligated using T4 DNA Ligase. DNA sequence analysis was performed to confirm the identity of the compact. This plasmid was transfected into HEX293T cells and a stably-transfected cell line (a pooled population) was isolated by drug selection as described by Donohue P J et al. (supra). The soluble Fn14-Fc protein was purified from conditioned medium by affinity chromatography as described by Donohue P J et al. (supra). Briefly, stably-transfected human 293T cells secreting the Fn14-Fc protein were cultured in growth medium containing 10% Ultra-low IgG FBS (Invitrogen) until they reached confluency and then conditioned medium was collected. Cells were removed by centrifugation and then the conditioned medium was incubated with protein A-Sepharose beads for 30 minutes at room temperature with end-over-end mixing. The beads were collected by a brief centrifugation and washed two times with PBS, once with 0.5 M NaCl in PBS, and once with PBS. The bound Fn14-Fc protein was eluted with 25 mM citrate buffer (pH 2.7) and then the eluate was neutralized with 1.5 M Tris/HCl pH 8.8, dialyzed against PBS, and concentrated in a Centricon-30 (Amicon).

The purity of the Fn14-Fc preparation was assessed by SDS-PAGE using 4-12% Bis-Tris NuPage gels (Invitrogen). Samples were either suspended in 2× gel loading buffer containing 10% 2-mercaptothanol (ME) and heated at 95° C. prior to loading (reducing conditions) or resuspended in 2× gel loading buffer without 2-ME and then loaded directly into the gel lanes (non-reducing conditions). Fn14-Fc was detected by staining the gel with 0.05% Coomassie Brilliant Blue R-250 (Kodak) and also by Western blot analysis. For Western blotting, Proteins were transferred to nitrocellulose membranes (Schleicher and Schuell, Keene, N.H.) and then visualized using Ponceau S Stain (Sigma, St Louis, Mo.). The membranes were blocked for 1 hour at 37° C. in TBST (25 mmol/L Tris/HCl pH 7.5, 150 mmol/L NaCl, 0.1% Tween-20) containing 5% nonfat dry milk and then incubated for 1 hour at room temperature in TBST containing 5% BSA and a 1:500 dilution of anti-myc monoclonal antibody 9E10 (gift of Sue Robinson, UMSOM). The membranes were then washed 3× with TBST, and incubated for 1 hour in TEST containing 5% nonfat dry milk and a 1:10000 dilution of horseradish peroxidase-conjugated goat anti-mouse IgG (Santa Cruz, Santa Cruz, Calif.). Membranes were washed 3× in TBST and bound secondary antibodies were detected using the Supersignal West Pico kit (Pierce, Rockford, Ill.).

Fn14-Fc was present in the conditioned medium as a ~80-kDa disulfide-linked dimer that could be converted to monomeric form using a reducing agent (FIG. 12A).

TWEAK binding to the Fn14-Fc fusion protein was demonstrated using an ELISA. Briefly, an ELISA plate was coated with either purified Fn 14-Fc protein or, as a control for non-specific binding, purified OPG-Fc protein (OPG is a natural decoy receptor for the TNF superfamily members RANKL and TRAIL) and then serial dilutions of FLAG epitope-tagged TWEAK were applied to the wells. This assay demonstrated that TWEAK specifically binds to the Fn14-Fc protein with an affinity constant (Kd) of ~1.1 nM (FIG. 12B).

Finally, the inhibition capability of the Fn14-Fc protein was tested, specifically inhibition of TWEAK activity in an endothelial cell (EC) proliferation assay. EC were incubated in basal medium containing 5% serum alone or 5% serum supplemented with either TWEAK, TWEAK plus a 25-fold molar excess of Fn14-Fc, TWEAK plus control IgG, Fn14-Fc alone, or control IgG alone. After three days of incubation, the cells were harvested and the cell number determined, TWEAK increased EC growth 1.6-fold under these experimental conditions, and this effect were significantly inhibited if the cytokine was first preincubated with the Fn14-Fc soluble receptor prior to its addition to the culture medium (FIG. 12C). This same concentration of Fn14-Fc protein had no significant affect on FGF-2- or VEGF-A-stimulated EC proliferation (FIG. 12D).

EXAMPLE 7

Effect of Fn14-Fc Decoy Receptor Administration on Ischemic Lesion Volume Following MCAO in the Mouse The role of TWEAK-Fn14 interactions in cerebral ischemia-mediated brain damage was examined using the soluble Fn14-Fc decoy receptor. For these studies, an additional plasmid that expresses the Fc portion and hinge region of the mouse IgG1 heavy chain was constructed. The Fc protein, which does not bind TWEAK, was purified from the conditioned medium of stably-transfected cells in the same manner as the Fn14-Fc decoy receptor (Donohue, P J., *Arterioscler. Thromb. Vasc. Biol.* 23:594-600 (2003)). Mice were placed on a stereotaxic frame immediately following MCAO and 2 µl of either PBS, soluble Fn14-Fc decoy receptor (1 µg/µl), or soluble Fc protein (1 µg/µl) was injected intraventricularly over a 60 second period using a Hamilton syringe. The coordinates for the injection were: bregma—2 mm, medial-lateral 0 mm and dorsoventral 2 mm (Paxinos, G. et al., *The Mouse Brain in Stereotaxic Coordinates*, Academic Press Inc., San Diego, Calif. 1-93 pp (2001)). After 72 hours, the brains were recovered and the volume of the ischemic lesion was quantified as described herein (see, for example Section 1).

Fn14-Fc decoy receptor administration resulted in an approximately 37% reduction in infarct volume, in contrast the Fc protein had no detectable effect (FIG. 13). These results are consistent with the findings of Potrovita, et al. (*J. Neurosci.* 24:8237-8244 (2004) using a different animal model of cerebral ischemia, who reported that the administration of anti-TWEAK neutralizing antibodies could also reduce infarct volume. Therefore, it appears that the intention between TWEAK and its receptor Fn14 is deleterious in cerebral ischemia. Moreover, our studies suggest that administration of the Fn14-Fc decoy receptor is a potential therapeutic strategy for the treatment of patients with acute ischemic stroke.

EXAMPLE 8

Effect of Fn14-Fc Decoy Receptor Administration on Ischemia-Induced Microglial Cell Activation in the Area of Ischemic Penumbra Microglial cells are resident brain macrophages in the CNS that respond to pathological events. In the first 24 hours following the onset of cerebral ischemia there is an increase in microglial cells in the area of the ischemic penumbra that persists for several days (Kato, H., et al., *Brain Res.*, 734:203-212 (1996); Lehrmann, E. et al., *Glia,* 24:437-448 (1998); and Zhang Z. et al., *Brain Res.,* 744:189-198 (1997)). Although resident microglial cells and blood-derived macrophages are virtually indistinguishable, it has been demonstrated that in the first 3-5 days following the onset of cerebral ischemia there are no blood-derived macrophages in the ischemic area (Stoll, G., et al., *Prog. Neurobiol.,* 56:149-171 (1998); and Schroeter M., et al., *Stroke,* 28:382-386 (1997)). Therefore, the applicants examined whether there was a reduction in microglial cell activation in the ischemic penumbra after administration of the Fn14-Fc decoy.

Immediately after MCAO, mice were placed in a stereotaxic frame and either PBS vehicle or the soluble Fn14-Fc decoy receptor were each adminstered via intraventricular injection at the same coordinates described above. Mice were sacrificed 72 hours later and immunohistochemistry was performed using an antibody that recognizes the integrin Mac-1 (αMβ2), a marker for microglial cells (Lee, Y. B. et al., *J. Neurosci. Res.,* 69:94-103(2002)). Treatment with the Fn14-Fc decoy receptor resulted in a significant decrease in the number of resident microglial cells in the ischemic penumbra following MCAO (FIG. 14). Applicants postulate that the protective effect observed after administration of Fn14-Fc decoy receptor may be due, at least in part, to Inhibition of the effects of TWEAK on microglial cells.

EXAMPLE 9

Effect of Fn14-Fc Decoy Receptor Administration on Ischemia-Induced Apoptotic Cell Death Several studies suggest that cell death in the area of ischemic penumbra evolves at a slower pace than in the necrotic core (Dirnagl, U., et al., *Trends Neurosci.*, 22:391-397 (1999)) and that cells in this area can survive for many hours or even days after the onset of the ischemic insult (Dereski M. O., et al., *Acta Neuropathol.* (*Berl*), 85:327-333 (1993)).

Likewise; multiple studies suggest apoptotic cell death may occur in the area of the ischemic penumbra (Garcia, et al. *Acta Neuropathol.* (Berl), 43:85-95 (1978); and Lee, J. M. et al., *Nature,* 399:A7-14 (1999)) in a process that is mediated by activation and cleavage of caspase-3 (Namura, S. et al., *J. Neurosci.*, 18:3659-3668 (1998)). Applicants contemplate that the TWEAK expressed in the brain in response to focal ischemia may either directly or indirectly induce cell death.

To study the role of TWEAK in ischemia induced apoptotic cell death in the area of ischemic penumbra; mice underwent MCAO followed by the intraventricular injection of either PBS vehicle or Fn14-Fc decoy receptor at the same coordinates described above. Animals were sacrificed 72 hours later and immunofluorescent TUNEL staining was performed. As previously reported by others (Garcia, et al., *Acta Neuropathol.* (Berl), 43:85-95 (1978), Aggoun-Zouaoui, D. et al., *Apoptosis*, 3:133-141 (1998), and Ruan, Y. W. et al., *Brain Res.*, 982:228-240 (2003)) a significant increase in the number of TUNEL positive cells was observed in the ischemic penumbra 72 hours after MCAO. However, treatment with the Fn14-Fc decoy receptor resulted in a significant decrease in the number of TUNEL positive cells in the sane area (FIG. 15). These results suggest that the interaction between TWEAK and Fn14 plays a role in ischemia induced cell death, and that Fn14-Fc decoy receptor delivery has a neuroprotective effect in the ischemic penumbra.

EXAMPLE 10

Effect of Fn14-Fc Decoy Receptor Administration on the Ischemia-Induced Increase in the Permeability of the Neurovascular Unit The neurovascular unit (NVU) is composed of endothelial cells, the vascular basement membrane and astrocytes, and is in direct contact with perivascular microglia and neurons. During cerebral ischemia there is an increase in the permeability of the NVU with passage of potentially harmful substances from the intravascular space into the brain and resultant vasogenic edema and cell death. It has been demonstrated that opening of the BBB following cerebral ischemia is induced by inflammatory cytokines including interleukin-1 (Bolton, S. J. et al., *Neuroscience,* 86:1245-1257 (1998)) and -8 (Matsumoto, T. et al., *Lab. Invest.*, 77:119-125 (1997))), as well as metalloproteases such as MMP-9 (Asahi, M. et al., *J. Cereb. Blood Flow Metab.,* 20:1681-1689 (2000); and Asahi, M. et al., *J. Neurosci.*, 21:7724-7732 (2001)) and it has been shown that induces IL-8 (Chicheportiche, Y. et al., *J. Biol. Chem.*, 272:32401-32410 (1997); Lynch, C. N. et al., *J. Biol. Chem.*, 274:8455-8459 (1999); Harada, N. et al., *Biochem. Biophys. Res. Commun.* 299:488-493 (2002); Nakayama, M et al., *J. Immunol,* 168:734-743 (2002); Nakayama, M. et al., *J. Immunol,* 170:341-348 (2003); and Kawakita, T. et al., *Biochem. Biophys. Res. Commun.*, 318:726-733 (2004)) and MMP-9 (Kim, S. H. et al., *Circ. J,* 68:396-399 (2004)) production in vitro. Thus, it is possible that the neuroprotective effect observed with the Fn14-Fc decoy receptor is due to inhibition of release of proinflammatory cytokines and MMP-9 and blockade of their known deleterious effects on BBB permeability (Asahi, M. et al., *J. Cereb. Blood Flow Metab.,* 20:1.681-1689 (2000); Asahi M. et al., *J. Neurosci.*, 21:7724-7732 (2001)). To test this hypothesis, animals underwent MCAO followed by intraventricular injection of either PBS, Fn14-Fc decoy receptor (2 ug) or control Fc protein (2 ug) and intravenous injection of Evans Blue dye, The brains were removed 72 hours later and Evans Blue dye extravasation was quantified as described previously (Yepes, M. et al., *J. Clin. Invest.*, 112:1533-1540 (2003)). Applicants demonstrated that cerebral ischemia-induced opening of the BBB was significantly attenuated by Fn14-Fc decoy receptor treatment (FIG. 22).

Consequently, Applicants disclose herein a therapeutic composition and method of using same for attenuating and/or preventing the opening of the BBB in neurological diseases associated with increase in the permeability of the NVU such as cerebral ischemia. The present invention also contemplates that TWEAK or Fn14 deficiency is protective in cerebral ischemia and that TWEAK inhibition by the administration of Fn14-Fc decoy receptor during the acute phase of cerebral ischemia is a therapeutic strategy aimed at preserving the integrity of the neurovascular unit and protecting neurons from the deleterious effects of cerebral ischemia.

EXAMPLE 11

Cell Cultures

Primary cerebral endothelial cell cultures: Brain capillary endothelia cells are isolated by a modification of a previously descried technique for bovine brains (Carson, M. P. et al., *In Vitro Cell Dev. Biol.*, 22:344-354 (1986)) that has also been successfully adapted for mice (Chem, Z., et al., *Lab. Invest.*, 78:353-363 (1998)). In brief the cerebral cortex of mice brains is aspirated and centrifuged. The tissue is homogenized, passed through nylon meshes, suspended after overnight digestion and placed on dishes coated with 1% gelatin. Twenty-four hours later, adherent cells are washed, fed with fresh Endothelial Cell Growth Media (Cell Applications Inc.) and treated several times with trypsin-EDTA, which results in selective release of endothelial cells. Endothelial cells are maintained on culture dishes in a humidified 5% $CO_2$-95% air incubator at 37° C. and passaged twice weekly using trypsin-EDTA. Experiments are performed on endothelial cells between passages 5 and 15. To confirm the presence of endothelial cells, methanol-fixed frozen slides are incubated with rabbit anti-VWF antibodies. Some slides are incubated with normal rabbit IgG as a control for nonspecific staining.

Primary astroyte and microglial cell cultures: Neonatal mouse glial cells are cultured from 1- to 2-day-old mice according to previously published procedures (McCarthy, K D. et al., *J. Cell Biol.,* 85:890-902 (1980)). In brief, cerebral hemispheres are removed and serially sieved trough meshes and the filtrate is centrifuged and re-suspended in DMEM. Cells are plated at a density of one brain/30 cm 2 and maintained in DMEM with 10% fetal bovine serum (PBS; Invitrogen) in a humidified 5% $CO_2$-95% air incubator at 37° C. At confluence, oligodendroglia are removed by orbital shaking. Glial cells are used between 20-40 days after birth. To confirm the presence of astocytes in our system, methanol-fixed frozen slides will be incubated with rabbit anti-GFAP antibodies. A monoclonal antibody directed against the Mac-1 integrin is used to detect microglial cells in these cultures. To detect active microglia, an antibody directed against ED1 (phagolysosomes) (Serotec Inc.) (Flaris, N. A. et al., *Glia,* 7:34-40 (1993)) is used.

Primary neuronal cultures: Primary neuronal cells are from mouse cortex at embryonic day 15 as described elsewhere (Bacskai, B. J. et al., *PNAS U.S.A.,* 97:11551-11556 (2000)). Briefly, the brain cortices are isolated in Ca +2-free PBS and homogenized in neurobasal medium containing 10% FBS, 2 mM glutamine, 100 U/ml penicillin, and 100 U/ml streptomycin (Invitrogen). The cells are plated onto polylysine-coated coverslips in 12-well tissue culture plates. After 60 minutes at 37° C., the medium is removed and attached cells are incubated in neurobasal medium. To confirm the presence of neurons in our cultures, the cells are stained with antiNeuN antibody (Chemicon).

EXAMPLE 12

In Vitro Blood Brain Barrier Model

Modified protocol is used for co-culture of cerebral endothelial cells and astrocytes (Minakawa, T. et al., *Lab. Invest.,* 65:32-40 (1991)). In brief to prepare capillary-like structures glass slides are coated with 1% gelatin and then add $4 \times 10^4$ endothelial cells/chamber in 1.0 mL DNBM with 2.5% equine serum. After 24 hours of incubation the cells are washed and 0.4 mL of a solution containing 80% type I collagen is added to the sub-confluent monolayer. The slides are incubated for 10 minutes at 37° C. and culture medium is added. Three days later, astrocytes ($4 \times 10^4$ cells/chamber), are added to the capillary preparations. It has been reported that astrocyte-endothelial cell co-cultures exhibit morphological features of the BBB seven days after co-culture initiation (Tran, N. D. et al., *Stroke,* 27:2304-2310 (1996)). Consequently, immunohistochemical analysis of gamma-glutamyl transpeptidase (GGTP), a putative marker of the BBB (Tran, N. D. et al., *J. Cereb. Blood Flow Metab.,* 1:1316-1324 (1998)), is monitored. GGTP staining is evident only when endothelial cell-astrocyte co-cultures develop features of the BBB Tran, N. D. et al., *Stroke,* 27:2304-2310 (1996)).

This in vitro model of the BBB as descried above was employed as described. Following a seven-day incubation, slides were histochemically stained for GGTP. The assay is based on the transfer of the glutamyl group from the substrate, gamma-glutamyl-4methoxy-2-napthylamide, to glycylglycine catalyzed by GGTP, using fast blue BB as the chromagen. The slides are fixed with 80% ethanol, then incubated at 37° C. for 90 minutes in a saline solution containing 0.25% DMSO, 1.2 mmol/L fast blue BB (Sigma), 0.125 mg/mL gamma-glutamyl-4-methoxy-2-napthylamide (Vega Biotechnologies), 20 mmol/L glycylglycine (Sigma), 2.5 mmol/L NaOH, and 25 mmol/L phosphate buffer. After incubation, the slides are washed in sate for 2 minutes, rinsed in 0.1 mol/L CuSO 4 for 2 minutes, washed again in saline for 2 minutes, and mounted. GGTP activity was evident as a brown stain.

GGTP activity is also measured using a standard assay kit (Sigma). In brief GGTP activity is quantified using a L-gamma-glutamyl-3-carboxy-4-nitroanilide (a colorless donor) and glycylglycine. GGTP catalyzes the transfer of the glutamyl group to yield 5-amino-2-nitrobenzoate, which absorbs light at 405 nm. The rate of absorbance is directly proportional to GGTP activity in the sample and absorbance is mea at 405 nm using a spectrophotometer. Units of GGTP activity are then normalized to cell number determined from parallel cultures in triplicate. In every case, rabbit anti-VWF factor and rabbit anti-GFAP antibodies is used to detect vascular endothelial cells and astrocytes, respectively. Experiments are carried out on day 12 of co-culture, 5 days after GTP staining is apparent.

EXAMPLE 13

Hypoxia Experiments

The present invention further contemplates that the TWEAK and Fn14 gene promoters may contain HIF-1 binding sites, and consequently the expression of these two genes may be regulated by hypoxia in vitro. Standard methods are available to determine the gene expression levels of TWEAK and Fn14, such as, for example, real-time quantitative RT-PCR, Western blot and ELISA assays.

Effect of hypoxia on TWEAK and Fn14 expression in monoculture systems: The appropriate cell types are isolated, cultured and then exposed to either hypoxic or hypoxic/glucose deprivation conditions in an anaerobic chamber (Bullups Rothember, Del Mar, Calif.) by adding either serum-lightened medium equilibrated with nitrogen (hypoxic medium) or serum-lightened and low glucose (0.2 g/L) medium equilibrated with nitrogen (OGD medium), for 0, 10, 30, 60 or 120 minutes. As controls (normoxic conditions), cells are placed in serum-lightened medium containing either 0.2 g/L or 1 g/L glucose and incubated under normal cell culture conditions (i.e., in a humidified 5% $CO_2$ incubator). After each time point the cells are harvested, culture medium is collected, and TWEAK and Fn14 expression analysis are performed.

Effect of hypoxia on TWEAK and Fn14 mRNA expression in an in vitro model of the blood brain barrier It has been demonstrated that the interaction between astrocytes and endothelial cells in the neurovascular unit plays an important regulatory role in the expression and activity of several proteins (Tran, N. D. et al, supra (1998), Tran, N. D. et al., supra (1999)). To determine the regulatory role for TWEAK and Fn14 interactions, in vitro preparations of the BBB are exposed to either normoxic, hypoxic, or hypoxic/glucose deprivation conditions for the predetermined periods of time. First, to examine the expression pattern of TWEAK and Fn14 in this co-culture system, cells are fixed and stained for TWEAK and Fn14 expression and co-stained with anti-VWF and anti-GFAP antibodies. Second, to study the effects of the interaction between astrocytes and endothelial cells an TWEAK and Fn14 mRNA levels under the same conditions, RNA is isolated from additional preparations obtained at similar time points and real-time RT-PCR analysis is performed to measure TWEAK and Fn14 mRNA levels as described below. Each sample is processed in triplicate and results are compared to normoxic controls obtained at each time point, as well as to results obtained from experiments performed in monoculture systems.

EXAMPLE 14

Gene Expression Assays

Real-time quantitative RT-PCR analysis: Quantitative RT-PCR analysis will be performed at each time point. Total. RNA is isolated using RNA Stat-60 (Tel-Test). One μg of each RNA sample is converted to cDNA using TaqMan Reverse Transcription Reagents (Applied Biosystems). Each PCR reaction is performed in triplicate using an ABI Prism 79001HT Sequence Detector System. The reactions comprise 5 μl of each cDNA, 1× TaqMan Universal PCR Master Mix, and murine TWEAK-, murine Fn14-, or rodent GAPDH-specific primers and fluorescent labeled probes (Applied Biosystems Assay-On-Demand Products) in 100 µl total volume. Threshold cycle (Ct) is obtained form the PCR reaction curves and TWEAK and Fn14 mRNA levels are quantitated using the comparative Ct method with GAPDH mRNA serving as the reference. Statistical significance of the differences between each sample and its respective control is evaluated with a Wilcoxon-two-sample rank sum test.

Western blot analysis: Western blot analysis is performed as previously described (Meighan-Mantha, R. L., et al., *J. Biol. Chem.*, 274:33166-33176 (1999)). In brief cells are harvested at the appropriate time points and lysed in 20 mM Tris-HCl pH 7.4, 150 mM NaCl, 1% Triton X-100, 2 mM EDTA, 1 mM DTT for 30 minutes on ice and spun at 13,000 rpm in a microcentrifuge for 5 minutes at 4° C. Protein concentrations are determined using the BCA protein assay kit (Pierce). Proteins are separated using SDS-PAGE and transferred to nitrocellulose membranes. The membranes are blocked in 5% milk in PBS with 0.1% Tween 20, and the blots will be probed overnight at 4° C. with anti-Fn14 (Meighan-Mantha, R. L., et al., supra (1999)) or anti-TWEAK (Cell Sciences) antibodies. The immunoblots are probed with horseradish peroxidase-conjugated anti-rabbit or anti-goat IgG secondary antibodies (Santa Cruz). Amer several washes, bound secondary antibodies are detected with an ECL kit (Amersham-Pharmacia Biotech).

ELISA: TWEAK levels in the culture medium are measured by ELISA as previously described (Kawakita, T. et al., *Biochem. Biophys. Res. Commun.*, 318:726-733 (2004)). Briefly when cells are harvested for the Western blot analysis, the culture supernatant is collected, centrifuged for 10 minutes, and the obtained supernatant is used for the experiments. 100 µl of antiTWEAK polyclonal antibody PeproTech) is added to each ELISA microplate well for coating. Culture medium at several dilutions is added to the wells. Recombinant TWEAK is used as a reference standard and serially diluted from 10 ng/ml to 0.25 ug/ml. Biotinylated anti-TWEAK antibody is added to each well and the plates incubated at room temperature for 2 hours. After washing, bound antibody is detected with avidin peroxidase and 2,20-AZINO-bis(3-ethylbenzthiazoline-6-sulfonic acid) substrate (Sigma). Color development is measured at 405 nm with a microtiter plate reader (Bio-Rad Laboratories).

EXAMPLE 15

Effects of TWEAK Treatment on the Cellular Components of the Neurovascular Unit and on the Integrity of the Blood Brain Barrier The present invention contemplates that following the onset of cerebral ischemia, TWEAK secreted from astrocytes interacts with Fn14 on microglial cells, and that this interaction results in NF-κB pathway activation with subsequent release of inflammatory cytokines and MMP-9 and resultant increases in BBB permeability and cell death. As disclosed herein, TWEAK treatment of microglial cells induced activation of the NF-κB pathway (FIG. 23) and injection of TWEAK directly into the cerebral cortex of healthy, non-ischemic animals resulted in increased permeability of the BBB (FIG. 16). Furthermore this effect was greatly enhanced in the presence of an ischemic signal. Accordingly, the following exemplary methods are contemplated for determining if exposure to TWEAK results in NF-κB pathway activation, expression of inflammatory cytokines and MMP-9, increase in BBB permeability and cell death.

To determine whether TWEAK treatment of glial cells and neurons induce NF-κB pathway activation, expression of inflammatory cytokines and MMP-9, and cell death in vitro monocultures of astrocytes, microglial cells, and neurons are prepared as described above. The monocultures are incubated with either PBS or recombinant TWEAK (0, 30, 100, 300 ng/ml; endotoxin-free; purchased from R&D Systems) in the presence of normoxic, hypoxic or hypoxic/glucose deprivation conditions. Cells are harvested after 0, 10, 30, 60 or 120 minutes and Western blot analysis is performed using antibodies that specifically recognize the phosphorylated form of IκBa as described (Donohue, P. J. et al., *Arterioscler. Thromb. Vasc. Biol.*, 23:594-600 (2003)). The phosphorylation of IκBa is an indicator of NF-κB activation.

In a parallel set of experiments, after each time point cells are harvested, RNA isolated and real-time RT-PCR analysis for IL-1, IL-6, IL-8, and MMP-9 mRNA expression is performed using TaqMan primers and reagents purchased from Applied Biosystems. The conditioned media is collected from these cells and can used for gelatin zymography (to measure NMP-9 activity) and ELISA assays (to measure IL-1, IL-6 and IL-8 protein levels) using commercially available kits from R & D Systems. A third group of cells is fixed at 0, 24, 48 or 72 hours and fluorescent TUNEL staining is performed (Chemicon) and caspase-3 activation will be evaluated using a FITC-conjugated anti-active caspase-3 antibody (BD PharMingen). The percentage of cells that are TUNEL positive or activated caspase-3 positive is calculated.

To determine whether TWEAK treatment induces disruption of the BBB in vitro, two approaches are contemplated. In the first approach the effects of TWEAK addition on the interaction between astrocytes and cerebral endothelial cells in an in vitro model of the neurovascular unit is employed. In the second approach TWEAK treatment of cerebral endothelial cells is performed and the degradation of tight junction (TJ), adherens junction (AJ), and/or cytoskeletal proteins is measured.

The presence of astrocytes in the BBB promotes the formation of tight junctions (Stewart, P. A. et al., *Dev. Biol.*, 84:183-192 (1981)) and the induction of GGTP. To study the effects of TWEAK on the integrity of the in vitro BBB model, co-cultures of endothelial cells and astrocytes are prepared as described above and incubated in the absence or presence of TWEAK (at the optimal dose determined above) for 0, 10, 30, 60 or 120 minutes. Similar experiments are performed on co-cultures exposed to hypoxic or hypoxic/glucose deprivation conditions for the same periods of time. At the end of each time point cell co-cultures are stained for GGTP as described above. If GGTP staining differences are observed, the amount of GGTP activity is measured.

To study the effect of TWEAK on the permeability of the BBB, the cytokine was injected d y into the mouse brain and the extravasation of Evans blue dye was quantified by spectrofluorophotometric analysis. It was found that the intracerebral injection of TWEAK results in a dose-dependent increase in the permeability of the BBB (FIG. 16). The recombinant TWEAK protein used in these experiments was purified from bacteria. To confirm that TWEAK and not containing bacterial endotoxin (lipopolysaccharide) was responsible for the observed effect, the TWEAK protein was incubated at 95° C. for 10 minutes prior to the intracerebral injection. No effect on BBB permeability was observed following the intracerebral injection of heat inactivated TWEAK (data not shown).

To investigate whether the observed effect of TWEAK on the permeability of the BBB was due to changes in the architecture of the NVU, either PBS or TWEAK was injected into the mouse brain and tissue was harvested 24 hours later. The architecture of the NVU was evaluated by immunogold electron microscopy. It was found that the intracererebral injection of TWEAK results in the accumulation of fluid in the perivascular space (FIG. 17b). This effect is associated with disruption of the glia limitans and detachment of the astrocytic foot processes with development of perivascular edema (FIG. 17d). These observations demonstrate that the effect of TWEAK on the permeability of the BBB is associated with structural changes in the architecture of the NVU.

EXAMPLE 16

Cerebral Endothelia Cells and Degradation

TWEAK treatment may induce degradation of TJ proteins ZO-1, ZO-2, occludin and claudin, the AJ protein vascular endothelial (VE)-cadherin or the cytoskeletal protein actin. To determine the effect of TWEAK on these proteins, mouse cortex-derived endothelial cell cultures is prepared and incubated in the absence or presence of TWEAK under either normoxic, hypoxic or hypoxic/glucose deprivation conditions. At the end of each time point cells are stained with antibodies that detect the TJ, AJ and cytoskeletal proteins. Applicants demonstrated that they could detect TJ proteins, VE-cadherin and actin under non-hypoxic conditions in cultured bovine brain microvascular endothelial cells. These cells were grown as described above. Cells were transferred to wells of a 24-well plate with coverslips containing either collagen or 0.1% gelatin to a final concentration of $1.2 \times 10^5$ cells per well. After confluence they were fixed with 10% buffered formalin and then stained with rabbit polyclonal anti-ZO-1, anti ZO-2, antioccludin antibodies (all three from Zymed Laboratories) and anti-VE-cadherin (Cayman Chemical Co.) antibodies. Goat anti-rabbit IgG (Alexa 488; Molecular Probes) was used as a secondary antibody. Control experiments were performed with similar conditions but using only the secondary antibody. Strong staining was observed for each of these proteins. Endothelial cell cultures fixed with formalin were also successfully stained for VE-cadherin and actin. To quantify the degradation of the cytoskeletal protein actin, cultures are stained for actin (with phalloidin) and viewed with a confocal scanning laser microscope. A fluorescent intensity histogram of a representative area is recorded, and the total intensity (gray scale value times the number of pixels that have that value) will be determined.

EXAMPLE 17

TWEAK Injection Induces NF-κB Activation, Expression of Rro-Inflammatory Cytokines and MMP-9, Opening of the BBB and Cell Death In Vivo Results indicate that injection of TWEAK directly into the healthy, nonischemic cortex results in an increase in BBB permeability (FIG. 16). To further characterize this effect, a dose-response curve for TWEAK-induced increase in BBB permeability is generated. Age- and sex-matched mice undergo an intracortical injection of either PBS or TWEAK (0, 2, 4, 10 μg) followed by intravenous administration of Evans blue dye. Mice are sacrificed 24 hours later and brains are analyzed for Evans blue dye extravasation. The dose determined to be most effective is administered. The effect of TWEAK on NF-κB activation is tested by administering either PBS or TWEAK directly into the cerebral cortex of age- and sex-matched wild-type or Fn14-deficient (Fn14−/−) mice under both non-ischemic or ischemic (MCAO) conditions. Brains are extracted at 0, 6, 24, 48 and 72 hours and 5 μm sections are stained for p65 translocation (NP-κB activation). A second experimental group of animals exposed to similar conditions can be sacrificed at the same time points, RNA is isolated from the ipsilateral (ischemic) and contralateral (non-ischemic) hemispheres and real-time RT-PCR for IL-1, IL-6, IL-8, and MMP-9 mRNA is performed. Optionally in a different experimental group of animals, brains are extracted at the same time points and gelatin zymographic assays for MMP-9 activity are performed (FIG. 3) (Yepes, M. et al., J. Clin. Invest., 112-1533-1540 (2003)).

To determine whether TWEAK could stimulate the NF-κB pathway in vivo, IκBα phosphorylation, an indicator of NF-κB pathway activation, was analyzed at 0, 1, 3 or 6 hours after the intracerebral injection of the cytokine. Brain lysates were prepared and Western blot analysis performed using appropriate antibodies. IκBα phosphorylation was found as early as one hour after treatment with TWEAK with a progressive decrease of total IκBα levels (FIG. 19a).

To determine what cell types in the brain were responding to TWEAK administration, TWEAK was injected into mouse brain. The brain tissue was harvested 6 hours later and subjected to immunofluorescence analysis using antibodies that recognize either neurons, microglia or astrocytes in combination with an anti-p65 antibody. TWEAK-induced translocation of the p65 subunit from the cytoplasm into the nucleus, an indicator of NF-κB pathway activation, was detected in the vast majority of astrocytes (FIGS. 23a-23f) and in some neurons (FIGS. 23g-23l), but in very few microglial cells (FIGS. 23m-23r).

It has been postulated that MMP-9 plays an important role in the proteolytic degradation of the NVU (Asahi et al., Stroke, 2000; Asahi et al., J. Cereb. Blood Flow Metab., 2001). To determine whether TWEAK can regulate MMP-9 activity in vivo, murine brains were injected with either TWEAK or PBS, tissue was harvested at 6, 12 or 24 hours and MMP-9 activity was analyzed by gelatin zymography assay. The applicants observed a progressive increase in MMP-9 activity in mice treated with TWEAK (FIG. 18, lanes 2-4), compared to PBS-injected mice (FIG. 18, lanes 5-7).

Since the immunofluorescence studies demonstrated that TWEAK acted primarily on astrocytes in vivo (FIG. 23), further studies were carried out to determine whether TWEAK treatment of cultured murine astrocytes increased MMP-9 activity. A significant increase in MMP-9 activity was detected in both the lysate and the media in TWEAK-treated astrocytes (FIG. 20, lanes 2 & 4). In contrast no MMP-9 activity was observed in PBS-treated cults (FIG. 20, lanes 3 & 5). These results demonstrate that TWEAK induces MMP-9 activation in astrocytes, and suggest that this activation may be responsible for the observed effect of TWEAK on the structure of the NVU and the permeability of the BBB.

To determine whether TWEAK-induced MMP-9 activation was mediated through the NF-κB pathway, MMP-9 activity was analyzed 24 hours after the intracerebral injection of TWEAK or PBS in wild-type and p50 deficient ($p50^{-/-}$) mice. An increase in MMP-9 activity was found in wild-type animals treated with TWEAK (FIG. 21a, lanes 2 & 3); in contrast, no MMP-9 activity was found in either wild-type mice treated with PBS (FIG. 21a, lanes 4 & 5) or in $p50^{-/-}$ animals treated with TWEAK (FIG. 21a, lanes 6 & 7) or PBS (FIG. 21a, lanes 8 & 9).

To study whether the observed increase in BBB permeability following treatment with TWEAK was also dependent on NF-κB pathway activation, the extravasation of Evans blue dye was quantified in wild-type and $p50^{-/-}$ mice 24 hours after the intracerebral injection of TWEAK. An increase in BBS permeability following the injection of TWEAK was observed in wild-type animals; in contrast, this effect was significantly decreased in p50$^{-/-}$ mice (FIG. 21b). Together, these data demonstrate that TWEAK induces MMP-9 activation in vivo through NF-κB, and suggest that this NF-κB-mediated activation of MMP-9 may result in degradation of the NVU.

Applicants have demonstrated that following the onset of cerebral ischemia there is a rapid increase in endogenous TWEAK expression (FIG. 8) and treatment with a soluble Fn14-Fc decoy receptor results in a decrease in the volume of the ischemic lesion (FIG. 13). FIG. 22 results support the hypothesis that increase in endogenous TWEAK following the onset of the ischemic insult causes disruption in the ultra-structure of the NVU with increase in the permeability of the BBB. To find out if the protection on the structure and permeability of the NVU provided by treatment with Fn14-Fc decoy had a correlation with clinical improvement following the ischemic insult, animals underwent MCAO followed by treatment with either Fn14-Fc decoy or Fc protein. An analysis of locomotor activity was performed before MCAO and at 6, 24 and 48 hours later. In each case, mice were placed on a locomotor activity box with an infrared device connected to a computer which detects and quantifies the vertical and horizontal movement of each animal (number of movements and total distance for each movement). Animals were sacrificed following the last evaluation on locomotor activity (48 hours after MCAO) and Evans blue dye extravasation was quantitated as described above. The results showed that treatment with Fn14-Fc decoy receptor resulted in significant decrease in cerebral ischemia-induced increase in BBB permeability (FIG. 24A, left panel). Moreover, compared to control animals, Fn14-Fc decoy-treated mice exhibited a faster recovery in locomotor activity at 24 and 48 hours which paralleled the severity of cerebral edema at 48 hours as measured by analysis of Evans blue dye extravasation (FIG. 24A, right panel). FIG. 24B shows the result from a similar experiment in which Fc and Fn14-Fc were administered 1 hour after onset of ischemia.

Applicants disclose herein, injection of TWEAK directly into the brain resulted in a increase in BBB permeability (FIG. 16). Additional experiments will be performed, involving injection of either PBS or TWEAK directly into the cerebral cortex of wild-type or Fn14-deficient (Fn14-/-) mice immediately after MCAO. Brains are extracted after 72 hours and the volume of the ischemic lesion is quantified. A different set of animals can undergo similar experimental conditions but followed by the injection of Evans blue dye. After 72 hours, animals are sacrificed and Evans blue dye extravasation in the ischemic hemisphere is quantified as previously described (87). Optionally, a third set of mice is sacrificed 72 hours after MCAO and immunostaining for TUNEL and caspase-3 activation is performed. Statistical analysis for all quantitative experiments will be performed.

EXAMPLE 18

Genetic Deficiency of TWEAK or Fn14 is Protective In Cerebral Ischemia

The brain inflammatory response to cerebral ischemia is characterized by the activation and proliferation of microglial cells, increased permeability of the neurovascular unit and cell death. Initial Fn14-Fc decoy experiments demonstrated that inhibition of TWEAK activity during cerebral ischemia is associated with a decrease in the volume of the ischemic lesion, attenuation of the infiltration of microglial cells into the area of ischemic penumbra, decrease in cerebral edema and inhibition of cell death.

To confirm the role of endogenous TWEAK and Fn14 in the pathogenesis of cerebral ischemia, animals deficient in either TWEAK or Fn14 (TWEAK -/- and Fn14-/- mice) may be used. The TWEAK and Fn14 knockout strains are viable, fertile and have no obvious phenotypic abnormalities.

In order to determine whether genetic deficiency of TWEAK or Fn14 results in a decrease in the volume of the ischemic lesion following MCAO in the mouse, age- and sex-matched wildtype, TWEAK -/- and Fn14-/- mice undergo MCAO. Brains are extracted 72 hours later and the volume of the ischemic lesion is measured. Different animal/genotype are used, such as, for example, a total of 10 animals/genotype in each group, and statistical analysis of the differences between the experimental groups is performed using the Wilcoxon-two sample sum test.

In order to determine if genetic deficiency of TWEAK or Fn14 is protective in cerebral ischemia-induced disruption of the BBB, two different approaches are contemplated. In one approach, Evans Blue dye extravasation is quantified following cerebral ischemia in wild-type, TWEAK -/- or Fn14-/- mice. In the second approach, the integrity of tight junction/adherens junction/cytoskeletal proteins during cerebral ischemia is examined. In order to observe the effect of genetic deficiency of TWEAK or Fn14 on Evans Blue dye extravasation following MCAO, wild-type, TWEAK -/- or Fn14-/- mice are subjected to MCAO followed by the intravenous injection of Evans Blue dye (20%). Brains are extracted after 6, 24, 48 and 72 hours, and Evans Blue dye extravasation is quantified as previously described (Yepes, M. et al., *J. Clin. Invest.*, 112:1533-1540 (2003)). For example, a total of 10 animals/genotype may used in each group and statistical analysis of the differences between the experimental groups will be performed using, for example, the Wilcoxon-two sample sum test.

Following the onset of cerebral ischemia there is degradation of tight junction/adherens junction and cytoskeletal proteins, with resultant increases in the permeability of the neurovascular unit. In this set of experiments, wild-type, TWEAK -/- and Fn14-/- mice will undergo MCAO. Brains are extracted following 0, 6, 24, 48 and 72 hours of cerebral ischemia, and 5 μm paraffin-embedded sections are obtained and stained for ZO-1, ZO-2, occludin, claudin-1, and VE-cadherin using the primary and secondary antibodies described earlier. Degradation of the cytoskeletal protein actin is also determined. The TJ, AJ and actin protein degradation is examined by Western blot analysis. In preliminary Western blot studies the four TJ proteins in murine brain extracts were detected. Thus, with this technique it is possible quantitate protein degradation by laser scanning densitometry.

The initial studies demonstrated that Fn14-Fc decoy receptor mediated inhibition of TWEAK activity results in a significant decrease in the number of both Mac-1 and TUNEL-positive cells in the area surrounding the necrotic core 72 hours after MCAO. In order to determine whether genetic deficiency of TWEAK or Fn14 inhibits cerebral ischemia-induced microglial cell activation and cell death, wild-type, TWEAK -/- or Fn14-/- mice undergo MCAO. Brains are extracted after 6, 24, 48 or 72 hours and sections obtained from the ischemic and non-ischemic areas are stained with antibodies that recognize either Mac-1 (microglia) or ED1 (active microglia). The number of Mac-1 and ED1 positive cells in cuts obtained at the same anatomic level are counted and results are compared to those obtained in either a corresponding area in the contralateral, nonischemic hemisphere, or to the ischemic area in wild-type mice. In each case, results are given as a ratio of total microglia/active microglial cells. To study the role of endogenous TWEAK or Fn14 in ischemia-induced cell death, wild-type, TWEAK −/− or Fn14−/− mice undergo MCAO. Brains are extracted and 5 um cuts are stained for TUNEL and active caspase-3. TUNEL and caspase-3 positive cells are counted at the same anatomic level and the results compared to the number of stained cells in the contralateral, non-ischemic hemisphere and the ischemic area of wild-type animals. For example, a total of 5 animals/genotype may be used in each experimental group and statistical analysis of the differences observed between groups is performed with the Wilcoxon-two sample sum test.

EXAMPLE 19

Mechanisms Responsible For the Protective Effect of Fn14 Fc Decoy Receptor and Combined Administration with tPA Applicants determined that treatment with Fn14-Fc decoy receptor following MCAO results in a significant decrease in the volume of the ischemic lesion and the severity of the disruption of the BBB, as well as in the extension of the microglial cell reaction and the number of cells with apoptotic features in the area of ischemic penumbra. Determination of the dose at which Fn14-Fc decoy receptor yields the maximum therapeutic benefit as measured by the volume of the ischemic area following MCAO is determined. In an exemplary method, the optimal therapeutic dose for Fn14-Fc decoy receptor is determined. For example, age- and sex-matched mice undergo MCAO followed by the intraventricular injection of either PBS vehicle or different doses (2 µg, 4 µg, 8 µg or 10 µg) of Fn14-Fc decoy receptor or the control Fc protein in a total volume of 2 µl. The injections are performed on a stereotaxic frame at the coordinates described above (Paxinos, G et al., *Academic Press Inc.*, San Diego, Calif. 1-93 pp (2001)). Brains are exacted at 72 hours and the volume of the ischemic lesion is measured as previously described (Yepes, M. et al., *Blood*, 96:569-576 (2000)). Once the optimal dose is determined, a different group of animals undergo MCAO followed byte admit ion of this dose of Fn14-Fc decoy receptor (and the control FE protein) trough either an intravenous (tail vein) or a subcutaneous (back) route. Animals are sacrificed at 72 hours and the volume of the ischemic lesion will be determined as described above. For example, a total of 5 or more animals may be used in each experimental group.

To study the effect of Fn14-Fc decoy receptor on NF-κB activation in viva, animals undergo MCAO followed by the administration of either PBS, Fn14-c decoy receptor, or control Fc protein at the dose and delivery route determined to be the optimal. Animals are sacrificed at 0, 12, 24 or 72 hours later and staining for p65 nuclear translocation (an indicator of NF-κB pathway activation) in ipsilateral (ischemic) and contralateral (nonischemic) hemispheres is conducted.

To observe the effect of Fn14-Fc decoy receptor on ischemia-induced pro-inflammatory cytokine and MMP-9 production, mice undergo MCAO followed by the administration of PBS, Fn14-Fc, or Fc as above. Animals are sacrificed at 0, 6, 24, 48 or 72 hours and RNA isolated from the non-ischemic or ischemic hemisphere are used for real-time RT-PCR experiments (IL-1, IL-6, IL-8, MMP-9). A different group of animals may be subjected to MCAO and treated as described above; brains extracted 0, 6, 24, 48 or 72 hours later and Evans Blue dye extravasation quantified as described elsewhere (Yepes, M. et al., *J. Clin. Invest.*, 112:1533-1540 (2003)). Finally, a fourth group of animals undergo MCAO and TUNEL and caspase-3 activation is detected in brain cuts extracted at 0, 24, 48, 72 or 96 hours. For example, a total of 5 or more animals can be used in each experimental group.

To determine whether the observed protective effect of Fn14-Fc decoy receptor administration on BBB breakdown can be exploited to prolong the therapeutic window for the administration of tPA without increasing the incidence of hemorrhagic complications, animals undergo embolic occlusion of the middle cerebral artery as described previously (Zhang, Z. et al. *Circulation*, 106:740-745 (2002)). At a predetermined time, i.e., three hours later, animals undergo administration of either PBS, Fn14-Fc, or control Fc protein at a predetermined dose via predetermined delivery route found to be effective. One hour later (4 hours after the onset of embolic stroke), animals are treated with an intravenous injection of tPA (Genentech Inc.) at a dose of 10 mg/kg (10% bolus and the remainder in a 30 minute interval). Two hours later (6 hours after the onset of the embolic lesion), diffusion-weighted images (DWI) are obtained as well as Gd-DTPA contrast multislice T1 weighted images. MRIs are performed. The progression of the ischemic lesion and the area of penumbra are evaluated by the relation between cerebral blood flow and apparent diffusion coefficient values as explained previously (Meng, X. et al., *Ann. Neurol.*, 55:207-212 (2004)). The volume of the ischemic lesion is measured from MRI parameters of DWI as described previously (Zhang, Z. et al., *Circulation*, 106:740-745 (2002)), and the leakage of the BBB is calculated from Gd-DTPA contrast MRI. Seventy-two hours later brains are extracted, and the volume of the ischemic lesion is measured as described previously (Yepes, M. et al., *Blood*, 96:569-576 (2000)). A subset of brains are embedded in paraffin and stained with hematoxylin & eosin to observe the presence of hemorrhagic transformation in the ischemic area. These results are compared to the data obtained with Gd-DTPA enhanced images. The skilled artisan is aware of methods and materials to determine experimental design such that the exemplary embodiments disclosed herein do not limit the scope of the present invention. For example, specifically, the administration of tPA can be 6 hours after the onset of the ischemic lesion, and an MRI will be performed 2 hours later.

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety. All of the following references have been cited in this application.

SEQ ID NO: 1 Murine Fn14 Extracellular (EC) Domain Sequence
APGTSPCSSGSSWSADLDKCMDCASCPARPHSDFCLGCAAAPPA SEQ ID NO: 2 Murine IgG Hinge and Fc Domain Sequence
LESSTKVDKKIVPRDCGCKPCICTVPEVSSVFIFPPKPKDVLTITLTPKV

TCVVVDISKDDPEVQFSWFVDDVEVHTAQTQPREEQFNSTFRSVSELPIM

HQDWLNGKEFKCRVNSAAFPAPIEKTISKTKGRPKAPQVYTIPPPKEQMA

KDKVSLTCMITDFFPEDITVEWQWNGQPAENYKNTQPIMDTDGSYFVYSK

LNVQKSNWEAGNTFTCSVLHEGLHNHHTEKSLSHSPGFGP

SEQ ID NO: 3 Myc Epitope Sequence
EQKLISEEDL

SEQ ID NO: 4 Histidine Tag Sequence
HHHHHH

SEQ ID NO: 5 Fn14-Fc Decoy Protein Entire Sequence
METDTLLLWVLLLWVPGSTGD*AAQPARRAAPGTSPCSSGSSWSADLDKC

MDCASCPARPHSDFCLGCAAAPPALESSTKVDKKIVPRDCGCKPCICTVP

EVSSVFIFPPKPKDVLTITLTPKVTCVVVDISKDDPEVQFSWFVDDVEVH

TAQTQPREEQFNSTFRSVSELPIMHQDWLNGKEFKCRVNSAAFPAPIEKT

ISKTKGRPKAPQVYTIPPPKEQMAKDKVSLTCMITDFFPEDITVEWQWNG

QPAENYKNTQPIMDTDGSYFVYSKLNVQKSNWEAGNTFTCSVLHEGLHNH

HTEKSLSHSPGFGPEQKLISEEDLNSAVDHHHHHH stop

*Signal peptide cleavage site

---

What is claimed is:

1. A method for treating a condition associated with an increase in blood brain barrier permeability selected from the group consisting of cerebral ischemia and a stroke, said method comprising:
   administering to a subject suffering from cerebral ischemia or a stroke an effective amount of an agent that disrupts interaction between the tumor necrosis factor-like weak inducer of apoptosis (TWEAK) protein and the fibroblast growth factor-inducible 14 (Fn14) receptor;
   wherein the agent is an Fn14 decoy receptor, an anti-TWEAK antibody, or an anti-Fn14 antibody.

2. The method of claim 1, wherein said agent is an isolated Fn14 decoy receptor.

3. The method of claim 1, wherein said Fn14 decoy receptor is soluble.

4. The method of claim 3, wherein said Fn14 decoy receptor comprises an extracellular domain of the Fn14 receptor.

5. The method of claim 4, wherein said Fn14 decoy receptor further comprises a fragment of an immunoglobulin.

6. The method of claim 5, wherein said fragment of an immunoglobulin includes the Fc portion and the hinge region of an IgG1 heavy chain.

7. The method of claim 4, wherein the Fn14 receptor is a human Fn14 receptor.

8. The method of claim 5, wherein said immunoglobulin is a human immunoglobulin.

9. The method of claim 1, wherein said agent is an anti-TWEAK or anti-Fn14 antibody.

10. The method of claim 9, wherein said antibody is a monoclonal antibody.

11. The method of claim 10, wherein said antibody is a humanized antibody.

12. The method of claim 1, further comprising co-administering to said subject tissue plasminogen activator (tPA) protein.

13. The method of claim 1, wherein the stroke is an ischemic stoke.

14. A method of treating a condition associated with an increase in blood brain barrier permeability selected from the group consisting of cerebral ischemia and stroke, said method comprising:
   administering to a subject suffering from cerebral ischemia or a stroke an effective amount of a Fn14 decoy receptor comprising: an extracellular domain of human Fn14 receptor; and an Fc portion and a hinge region of a human IgG1 heavy chain, wherein said Fn14 decoy receptor disrupts interaction between a TWEAK protein and a Fn14 receptor.

15. A method of treating a stroke, said method comprising:
   administering to a subject in need thereof an effective amount of a Fn14 decoy receptor comprising an extracellular domain of human Fn14 receptor and an Fc portion and a hinge region of a human IgG1 heavy chain;
   wherein said Fn14 decoy receptor disrupts interaction between a TWEAK protein and a Fn14 receptor.

16. A method for treating a condition associated with an increase in blood brain barrier (BBB) permeability selected from the group consisting of cerebral ischemia and a stroke, said method comprising administering to a subject in need thereof an effective amount of an agent that inhibits activity of a TWEAK protein in the brain of the subject;
   wherein the agent is an Fn14 decoy receptor, an anti-TWEAK antibody, or an anti-Fn14 antibody.

17. The method of claim 16, wherein the stroke is an ischemic stroke.

18. The method of claim 16, wherein the inhibition of said activity of the TWEAK protein comprises inhibition of TWEAK expression.

19. A method for treating a condition associated with an increase in blood brain barrier permeability selected from the group consisting of cerebral ischemia and a stroke, said method comprising:
   administering to a subject suffering from cerebral ischemia or a stroke an effective amount of an agent that inhibits Fn14 signal transduction;

wherein the agent is an Fn14 decoy receptor, an anti-TWEAK antibody, or an anti-Fn14 antibody.

20. The method of claim 19, wherein the stroke is an ischemic stroke.

21. A method for treating a condition associated with an increase in blood brain barrier permeability selected from the group consisting of cerebral ischemia and stroke, said method comprising:

administering to a subject suffering from cerebral ischemia or stroke an effective amount of an agent that inhibits Fn14 receptor expression;

wherein the agent is an Fn14 decoy receptor, an anti-TWEAK antibody, or an anti-Fn14 antibody.

22. The method of claim 21, wherein the stroke is an ischemic stroke.

23. The method of claim 1, wherein the agent is administered by intraventricular injection near the blood brain barrier.

24. The method of claim 16, wherein the agent is administered by intraventricular injection near the blood brain barrier.

25. The method of claim 19, wherein the agent is administered by intraventricular injection near the blood brain barrier.

26. The method of claim 21, wherein the agent is administered by intraventricular injection near the blood brain barrier.

* * * * *